US012702660B2

(12) United States Patent
Xiao et al.

(10) Patent No.: US 12,702,660 B2
(45) Date of Patent: Aug. 11, 2026

(54) METHOD FOR TREATING CANCER WITH AN ORAL DOSAGE FORM OF AN ESTROGEN RECEPTOR-ALPHA INHIBITOR

(71) Applicant: Eisai R&D Management Co., Ltd., Tokyo (JP)

(72) Inventors: Jianjun Xiao, Lexington, MA (US); Nathalie M. Rioux, Woburn, MA (US); Victoria Rimkunas, Reading, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 1178 days.

(21) Appl. No.: 17/613,681

(22) PCT Filed: May 15, 2020

(86) PCT No.: PCT/US2020/033292

§ 371 (c)(1),
(2) Date: Nov. 23, 2021

(87) PCT Pub. No.: WO2020/242795

PCT Pub. Date: Dec. 3, 2020

(65) Prior Publication Data

US 2022/0226300 A1 Jul. 21, 2022

Related U.S. Application Data

(60) Provisional application No. 62/853,498, filed on May 28, 2019, provisional application No. 62/852,751, filed on May 24, 2019.

(51) Int. Cl.
*A61K 31/4439* (2006.01)
*A61K 9/48* (2006.01)
*A61P 35/00* (2006.01)

(52) U.S. Cl.
CPC ........ *A61K 31/4439* (2013.01); *A61K 9/4858* (2013.01); *A61K 9/4866* (2013.01); *A61P 35/00* (2018.01)

(58) Field of Classification Search
CPC .................................................. A61K 31/4439
See application file for complete search history.

(56) References Cited

U.S. PATENT DOCUMENTS

| | | | |
|---|---|---|---|
| 9,796,683 | B2 | 10/2017 | Bock et al. |
| 2016/0347717 | A1 | 12/2016 | Bock et al. |

FOREIGN PATENT DOCUMENTS

| | | | | |
|---|---|---|---|---|
| EA | 028301 B1 | 10/2017 | | |
| KR | 10-2018-0011274 A | 1/2018 | | |
| WO | WO-2014136048 A1 * | 9/2014 | ......... | A61B 17/1204 |
| WO | 2015165847 A1 | 11/2015 | | |
| WO | 2018049042 A1 | 3/2018 | | |
| WO | 2018097273 A1 | 5/2018 | | |

OTHER PUBLICATIONS

Ge et al., 2019, Journal of Pharmaceutical and Biomedical Analysis, 172, 189-199 (Year: 2019).*

Brown, W., Pharmaceutical Dosage Forms, Pharmacopeial Forum, 35(5), Sep.-Oct. 2009 (Year: 2009).*

DTP/DCTD/NCI/NIH/DHHS, Equivalent Surface Area Dosage Conversion Factors, Aug. 2007, http://dtp.nci.nih.gov (Year: 2007).*

Rowe, R. C., Sheskey, P. J., & Owen, S. C. (2009). Handbook of Pharmaceutical excipients (6th ed.). APhA/Pharmaceutical Press (Year: 2009).*

International Search Report (PCT/ISA/210) and Written Opinion (PCT/ISA/237) mailed on Aug. 5, 2020, by the European Patent Office as the International Searching Authority for International Application No. PCT/US2020/033292.

Rioux, Nathalie, et al., "Nonclinical pharmacokinetics and in vitro metabolism of H3B-6545, a novel selective ER[alpha] covalent antagonist (SERCA)", Cancer Chemotherapy and Pharmacology, Nov. 1, 2018, vol. 83, No. 1, pp. 151-160. (10 pages).

Anonymous, "NCT03250676: Trial of H3B-6545, in Women With Locally Advanced or Metastatic", Estrogen Receptor-positive, HER2 Negative Breast Cancer, Jan. 29, 2019, retrieved from the internet: https://clinicaltrials.gov/ct2/history/NCT03250676?V_8=View#StudyPageTop. (4 pages).

Hamilton, Erika Paige, et al., "Phase I dose escalation of H3B-6545, a first-in-class highly Selective ER[alpha] Covalent Antagonist (SERCA), in women with ER-positive, HER2-negative breast cancer (HR+ BC).", Journal of Clinical Oncology, May 20, 2019. (5 pages).

Krasnyuk et al., "Pharmaceutical Technology", Pharmaceutical Dosage Forms, 2006, 2nd edition, with machine English translation. (6 pages).

Leung et al., "Relationship Between Signaling Pathway Usage and Sensitivity to a Pathway Inhibitor: Examination of Trametinib Responses in Cultured Breast Cancer Lines", PLOS ONE, Aug. 2014, vol. 9, No. 8. (12 pages).

Office Action issued on Oct. 23, 2023, by the Russian Patent Office in corresponding Russian Patent Application No. 2021138145/04, and an English Translation of the Office Action. (31 pages).

ASCO 2019 Poster Session (Board #140), Sun, 8:00 AM-11:00 AM, Abstract 1059, Jun. 2, 2019, "Phase 1 Dose Escalation of H3B-6545, a first-in-class highly Selective ERα Covalent Antagonist (SERCA), in Women with ER-positive, HER2-negative Breast Cancer (HR+ BC)", Breast Cancer-Metastatic, Erika Paige Hamilton, Tennessee Oncology, PLLC and Sarah Cannon Research Institute, Nashville, TN.

ASCO Genomics Poster 1052, Jun. 2, 2019: "Molecular Characterization and Monitoring of Patient ctDNA in Phase I Study of H3B-6545 in ER+ MBC", Vicki Rimkunas et al.

(Continued)

*Primary Examiner* — John S Kenyon
*Assistant Examiner* — Sara Elizabeth Bell
(74) *Attorney, Agent, or Firm* — BUCHANAN INGERSOLL & ROONEY PC

(57) ABSTRACT

The present invention relates to pharmaceutical compositions comprising an inhibitor of human ERα, and methods of cancer therapy using the ERα inhibitor. In particular, described herein are dosages of H3B-6545 with defined pharmacokinetic (PK) profiles that allow the inhibitor to be efficaciously and safely administered to a human subject in need thereof.

18 Claims, 8 Drawing Sheets

(56) References Cited

OTHER PUBLICATIONS

ASCO 2019 Poster Abstract 1059, May 15, 2019, "Phase 1 Dose Escalation of H3B-6545, a First-in-Class Highly Selective ERα Covalent Antagonist (SERCA), in Women with ER-positive, HER2-negative Breast Cancer", Erika Hamilton, MD, et al.
ASCO 2019 Proceedings Abstract 1052, May 15, 2019: "Molecular characterization and monitoring of patient ctDNA in phase I study of H3B-6545 in ER+ MBC", Vicki Rimkunas, H3 Biomedicine, Cambridge, MA.
Bolshakov, V. I. "Excipients in the technology of dosage forms" Leningrad, 1991, 5 pages. (with partial English translation).
Tentsova, A. I. et al. "Modern biopharmaceutical aspects of excipients" Pharmacy, N 7, 2012, 5 pages. (with partial English translation).
Office Action issued on Jun. 14, 2024, by the Federal Service for Intellectual Property in Russian Patent Application No. 2021138145/04 and an English Translation of the Office Action, (27 pages).
Office Action (Notice of Preliminary Rejection) issued on Aug. 22, 2025, by the Intellectual Property Office in corresponding Korean Patent Application No. 10-2021-7041807, and an English Translation of the Office Action. (14 pages).

* cited by examiner

| Mutations | Present in Tissue Biopsy | Not Present in Tissue Biopsy |
|---|---|---|
| Present in Liquid Biopsy | 16 | 15 |
| Not Present in Liquid Biopsy | 4 | 0 |

METHOD FOR TREATING CANCER WITH AN ORAL DOSAGE FORM OF AN ESTROGEN RECEPTOR-ALPHA INHIBITOR

CROSS-REFERENCE TO RELATED APPLICATIONS

This application claims benefit of U.S. Provisional Patent App. No. 62/852,751, filed on May 24, 2019, and U.S. Provisional Patent App. No. 62/853,498, filed on May 28, 2019. Those applications are incorporated by reference as if fully rewritten herein.

BACKGROUND OF THE INVENTION

Altered estrogen receptor (hereinafter ER) signaling is known to play a key role in the development of various types of breast cancers. The activation of ER signaling typically relies on the expression and ability of endogenous steroid hormones, such as estradiol, to penetrate into a cell and interact with intracellular ERs. Once activated, ER signaling promotes a variety of cellular processes such as proliferation, angiogenesis, metabolism and cell survival (Toss A. et al. 2017*, Int. J. Mol. Sci.,* 18(1):85). During tumorigenesis, it is a common occurrence for mutations to develop within different ERs, wherein said mutations grant cancer cells the ability to activate ER signaling pathways in ligand-independent manners. A specific ER known to be involved in the tumorigenesis of breast cancers, ERα, is a hormone-regulated transcription factor that is present in 50% of all breast cancers (Lumachi F., *Curr. Med Chem.* 2013; 20:596-604).

Expression of estrogen receptor alpha (ERα, ESR1), a hormone-regulated transcription factor, occurs in approximately 70% of breast cancers. Lumachi F., *Curr. Med. Chem.* 2013; 20:596-604. A number of ERα-directed therapies have been developed. Resistance to ERα antagonists is common in the clinic involving several mechanisms. One mechanism, ERα mutations, occurs in 20-40% of endocrine-therapy resistant metastases. Li S, *Cell Rep.* 2013; 4:1116-1130; Robinson D R, *Nat Genet.* 2013; 45:1446-1451; Toy W, *Nat Genet.* 2013; 45:1439-1445; Chandarlapaty S, JAMA *Oncol.* 2016; 2:1310-1315; Spoerke J M, *Nat Commun.* 2016; 7:11579. Mutations in ERα lead to ligand-independent activation of the ERα pathway.

Endocrine therapies are at the forefront of treatment methods employed to treat or cure breast cancers. Endocrine therapies are those that involve promoting or inhibiting the expression or functions of hormones within the body to treat a particular disease. Endocrine therapies targeting ERα have been shown to be ineffective in long-term treatment methods for breast cancers since between 20% to 40% of all breast cancers expressing ERα acquire a mutation within ERα after prolonged endocrine therapy, said mutations rendering the receptor unresponsive to conventional endocrine therapies (Robinson, D. R., *Nat. Genet.* 2013; 45:1446-1451). Hence, there is a need in the chemotherapeutics field to develop new treatment methods that are able to effectively target mutated isoforms of ERα that render cancers endocrine therapy resistant.

During the pursuit to develop new treatment methods for endocrine therapy resistant breast cancers, a new class of ERα inhibitors, called Selective Estrogen Receptor Covalent Antagonists (hereinafter SERCAs), were discovered. SERCAs inactivate ER signaling by targeting a cysteine residue on the ERs that is not present in other nuclear hormone receptors (Puyang, X., *Cancer Discov.* 2018, 8(9): 1176-1193). One of the SERCAs that emerged during this time was (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide, which is shown below in Formula I:

(Formula I)

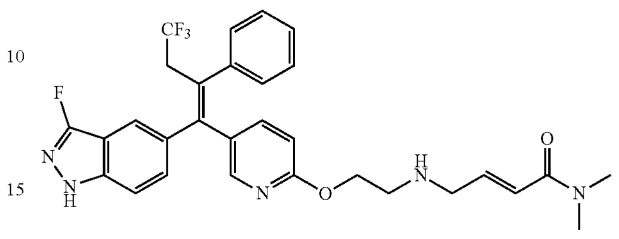

(E) -N,N-dimethyl-4-[2-[5-[(Z)-4,4,4-trifluoro-1-(3 -fluoro-1H-indazol-5-yl)-2-phenylbut-1-enyl)pyridin-2-yl)oxyethylamino]but-2-enamide The free base form of (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide is sometimes referred to as H3B-6545. H3B-6545 is a covalent small-molecule inhibitor that inactivates both wild-type ERα (ERα-WT) and mutant ERα (ERα-mut) without degrading the receptor. H3B-6545 is able to interact with ERα's Cys530 residue, which causes the receptor to adopt a unique conformation that inhibits the receptor's ability to promote ligand-independent ERα signaling transduction (Puyang, X., *Cancer Discov.* 2018, 8(9):1176-1193). H3B-6545 has been shown to elicit potent chemotherapeutic properties in various breast cancer cell lines and patient-derived xenograft models in nude mice (Smith, P. G., et al., *Cancer Res.* 2017).

Though H3B-6545 has been shown to be effective in in vitro and in vivo models, the manner by which H3B-6545 should be administered to a human breast cancer patient in need of treatment has yet to be determined. Hence, there is a need to devise a formulation and dosage regimen of H3B-6545 that will allow the inhibitor to be more efficaciously and safely administered to human subjects in need thereof. Characterizing pharmacokinetic (hereinafter PK) outcomes and PK profile later affords their general use in human breast cancer treatment methods.

BRIEF SUMMARY

Embodiments may provide, for example, an oral dosage form comprising a compound given by Formula I or a pharmaceutically acceptable salt thereof, and at least one pharmaceutically acceptable excipient, wherein said Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide; wherein said oral dosage form when administered orally once daily to a human subject is formulated to achieve a mean $C_{max}$ of about 1 ng/mL to about 4 ng/mL as measured for every mg of Formula I in said dosage. In some embodiment said mean $C_{max}$ is about 2 ng/mL to about 4 ng/mL for every mg of Formula I in said dosage. In some embodiments said mean $C_{max}$ is about 3 ng/mL to about 4 ng/mL for every mg of Formula I in said dosage. In some embodiments said mean $C_{max}$ is in the range of 80% to 125% of 3 ng/mL to 80% to 125% of 3.5 ng/mL for every mg of Formula I in said dosage.

In further embodiments the dosage form is formulated to achieve a mean tmax of said mean $C_{max}$ in about 2 hours to about 7 hours. In further embodiments the dosage form is formulated to achieve a mean $t_{max}$ of said mean $C_{max}$ in about 3 hours to about 7 hours. In further embodiments the dosage form is formulated to achieve a mean $t_{ma}x$ of said mean $C_{max}$ in about 3.5 hours to about 4.5 hours. In further embodiments the dosage form is formulated to achieve a mean $t_{max}$ of said mean $C_{max}$ in about 5.5 hours to about 6.5 hours.

In some embodiments as reported above, the dosage form comprises a total equivalent of about 100 mg to about 600 mg of Formula I. In some embodiments the dosage form comprises a total equivalent of about 450 mg of Formula I.

Further embodiments provide an oral dosage form comprising a compound given by Formula I or a pharmaceutically acceptable salt thereof and at least one pharmaceutically acceptable excipient, where said Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide, and wherein said oral dosage form when administered orally once daily to a human subject is formulated to achieve a mean AUC0-24 of about 16 h*ng/mL to about 44 h*ng/mL for every mg of Formula I in said dosage. In some embodiments said mean AUC0-24 is about 27 h*ng/mL to about 44 h*ng/mL for every mg of Formula I in said dosage. In some embodiments said mean AUC0-24 is in the range of 80% to 125% of 30 h*ng/mL to 80% to 125% of 44 h*ng/mL for every mg of Formula I in said dosage. In some embodiments the dosage form comprises a total equivalent of about 100 mg to about 600 mg of Formula I. In some embodiments the dosage form comprises a total equivalent of about 450 mg of Formula I.

Further embodiments provide an oral dosage form comprising a compound given by Formula I or a pharmaceutically acceptable salt thereof and at least one pharmaceutically acceptable excipient, wherein said compound given by Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide, and wherein said oral dosage form when administered orally once daily to a human subject is formulated to achieve a mean $t_{1/2}$ of Formula I of said dosage of about 8 hours to about 22 hours. In further embodiments the mean tin is about 8 hours to about 12 hours. In further embodiments the mean tin is about 9 hours to about 11 hours. In some embodiments the dosage form comprises a total equivalent of about 100 mg to about 600 mg of Formula I. In some embodiments the dosage form comprises a total equivalent of about 450 mg of Formula I.

Further embodiments provide an oral dosage form comprising a compound given by Formula I or a pharmaceutically acceptable salt thereof and at least one pharmaceutically acceptable excipient, wherein said compound given by Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide, and wherein said oral dosage form when administered orally once daily to a human subject is formulated to achieve a mean $AUC_{0\text{-}inf\ of\ about}$ 21 h*ng/mL to about 67 h*ng/mL for every mg of Formula I in said dosage. In some embodiments the mean $AUC_{0\text{-}inf}$ is about 29 h*ng/mL to about 67 h*ng/mL for every mg of Formula I in said dosage. In some embodiments the mean $AUC_{0\text{-}inf}$ is in the range of 80% to 125% of 36 h*ng/mL to 80% to 125% of 57 h*ng/mL for every mg of Formula I in said dosage. In some embodiments the dosage form comprises a total equivalent of about 100 mg to about 600 mg of Formula I. In further embodiments the dosage form comprises a total equivalent of about 450 mg of Formula I.

Still further embodiments may include dosage forms as described herein, having means to achieve the pharmacokinetic values described herein.

A further embodiment provides an oral dosage form comprising a compound given by Formula I or a pharmaceutically acceptable salt thereof and at least one pharmaceutically acceptable excipient, wherein said compound of Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide and wherein said oral dosage form when administered orally once daily to a human subject is formulated to achieve a mean $AUC_{0\text{-}t}$ of about 16 h*ng/mL to about 41 h*ng/mL for every mg of Formula I in said dosage. In a further embodiment said mean $AUC_{0\text{-}t}$ is in the range of 80% to 125% of 27 h*ng/mL to 80% to 125% of 36 h*ng/mL for every mg of Formula I in said dosage. In a further embodiment said dosage form comprises a total equivalent of about 100 mg to about 600 mg of Formula I. In a further embodiment said dosage form comprises a total equivalent of about 450 mg of Formula I.

In further embodiments, dosage forms as previously reported may be a capsule comprising an internal phase comprising Formula I or a pharmaceutically acceptable salt, lactose monohydrate, low-substituted hydroxypropyl cellulose, microcrystalline cellulose, hydroxypropylcellulose, colloidal anhydrous silica, and magnesium stearate; and an external phase comprising magnesium stearate. In some embodiments the capsule is a hypromellose capsule. In some embodiments the capsule includes a mono-HCl salt form of Formula I.

In some embodiments as previously reported, said oral dosage form is a tablet comprising an internal phase comprising Formula I or a pharmaceutically acceptable salt, lactose monohydrate, low-substituted hydroxypropyl cellulose, hypromellose, colloidal silicon dioxide and purified water; an external phase comprising microcrystalline cellulose and magnesium stearate; and a film coating comprising hypromellose, talc, titanium dioxide, propylene glycol, ferric oxide and purified water. In further embodiments the table comprises a mono-HCl salt form of Formula I.

Further embodiments provide a method of treating cancer in a human subject comprising administering to said subject an oral dosage form comprising a therapeutically effective amount of a compound given by Formula I or a pharmaceutically acceptable salt thereof at least one pharmaceutically acceptable excipient, wherein said Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide, wherein said therapeutically effective amount is a single daily dose ranging from about 100 mg to 600 mg and wherein said oral dosage form has a mean $C_{max}$ of about 1 ng/mL to about 4 ng/mL in the blood plasma of said subject for every mg of Formula I in said dosage. In some embodiments said mean $C_{max}$ is about 2 ng/mL to about 4 ng/mL for every mg of Formula I in said dosage. In some embodiments said mean $C_{max}$ is about 3 ng/mL to about 4 ng/mL for every mg of Formula I in said dosage. In some embodiments said mean $C_{max}$ is in the range of 80% to 125% of 3 ng/mL to 80% to 125% of 3.5 ng/mL for every mg of Formula I in said dosage. In some embodiments the dosage form has a mean $t_{max}$ of said mean $C_{max}$ of Formula I of about 2 hours to about 7 hours. In some embodiments the dosage form has a mean $t_{max}$ of said mean $C_{max}$ of Formula I of about 3 hours to about 7 hours. In some embodiments the dosage form has a mean $t_{max}$ of said mean $C_{max}$ of Formula I of about 3.5 hours to about 4.5 hours. In some embodiments the dosage form has a mean $t_{max}$ of said mean $C_{max}$ of Formula I of about 5.5 hours to about 6.5 hours.

Further embodiments may provide a method of treating cancer in a human subject comprising administering to said subject an oral dosage form comprising a therapeutically effective amount of a compound given by Formula I or a pharmaceutically acceptable salt thereof and at least one pharmaceutically acceptable excipient, wherein said compound given by Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide and wherein said oral dosage form has a mean $AUC_{0-24}$ of about 16 h*ng/mL to about 44 h*ng/mL for every mg of Formula I in said dosage. In further embodiments said mean $AUC_{0-24}$ is about 27 h*ng/mL to about 44 h*ng/mL for every mg of Formula I in said dosage. In further embodiments said mean AUC0-24 is in the range of 80% to 125% of 30 h*ng/mL to 80% to 125% of 44 h*ng/mL for every mg of Formula I in said dosage.

Further embodiments provide a method of treating cancer in a human subject comprising administering to said subject an oral dosage form comprising a therapeutically effective amount of a compound given by Formula I or a pharmaceutically acceptable salt thereof and at least one pharmaceutically acceptable excipient, wherein said compound of Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide and wherein said oral dosage form has a mean tin of about 8 hours to about 22 hours. In some embodiments said mean tin is about 8 hours to about 12 hours. In some embodiments said mean tin is about 9 hours to about 11 hours.

Further embodiments provide a method of treating cancer in a human subject comprising administering to said subject an oral dosage form comprising a therapeutically effective amount of a compound given by Formula I or a pharmaceutically acceptable salt thereof and at least one pharmaceutically acceptable excipient, wherein said compound of Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide and wherein said oral dosage form has a mean $AUC_{0-inf}$ of about 21 h*ng/mL to about 67 h*ng/mL for every mg of Formula I in said dosage. In some embodiments said mean $AUC_{0-inf}$ is about 29 h*ng/mL to about 67 h*ng/mL for every mg of Formula I in said dosage. In some embodiments the mean $AUC_{0-inf}$ is in the range of 80% to 125% of 36 h*ng/mL to 80% to 125% of 57 h*ng/mL for every mg of Formula I in said dosage.

Further embodiments provide a method of treating cancer in a human subject comprising administering to said subject an oral dosage form comprising a therapeutically effective amount of a compound given by Formula I or a pharmaceutically acceptable salt thereof and at least one pharmaceutically acceptable excipient, wherein said compound of Formula I is (E)-N,N-dimethyl-4-[2-[5-[(Z)-4,4,4-trifluoro-1-(3-fluoro-1H-indazol-5-yl)-2 -phenylbut-1-enyl]pyridin-2-yl]oxyethylamino]but-2-enamide and wherein said oral dosage form has a mean $AUC_{0-t}$ of about 16 h*ng/mL to about 41 h*ng/mL for every mg of Formula I in said dosage. In further embodiments the mean $AUC_{0-t}$ is in the range of 80% to 125% of 27 h*ng/mL to 80% to 125% of 36 h*ng/mL for every mg of Formula I in said dosage.

In some embodiments of methods reported herein, a dosage form comprises a total equivalent of about 100 mg to about 600 mg of Formula I. In other embodiments a dosage form comprises a total equivalent of about 200 mg to about 600 mg of Formula I. In other embodiments said dosage form comprises a total equivalent of about 300 mg to about 600 mg of Formula I. In other embodiments said dosage form comprises a total equivalent of about 450 mg of Formula I.

In some embodiments of methods reported herein the oral dosage form is a capsule comprising an internal phase comprising a compound of Formula I or a pharmaceutically acceptable salt, lactose monohydrate, low-substituted hydroxypropyl cellulose, microcrystalline cellulose, hydroxypropylcellulose, colloidal anhydrous silica, and magnesium stearate; and an external phase comprising magnesium stearate. In some embodiments the capsule is a hypromellose capsule. In some embodiments the capsule includes a mono-HCl salt form of Formula I.

In some embodiments as reported herein the oral dosage form is a tablet comprising an internal phase comprising a compound of Formula I or a pharmaceutically acceptable salt, lactose monohydrate, low-substituted hydroxypropyl cellulose, hypromellose, colloidal silicon dioxide and purified water; an external phase comprising microcrystalline cellulose and magnesium stearate; and a film coating comprising hypromellose, talc, titanium dioxide, propylene glycol, ferric oxide and purified water. In some embodiments the tablet includes a mono-HCl salt form of Formula I.

In some embodiments of methods reported herein the cancer is breast cancer. In some embodiments the breast cancer is an ERα-positive breast cancer. In some embodiments the breast cancer expresses wild-type ERα. In some embodiments the breast cancer expresses a mutant ERα.

In some embodiments as reported herein, said oral dosage form is administered once daily. In some embodiments said oral dosage form is administered to the human in a fasted state. In some embodiments said oral dosage form is administered to the human in a fed state.

Embodiments provide a method of treating a patient with compound H3B-6545:

(H3B-6545)

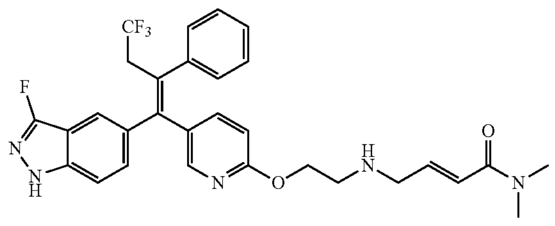

or a pharmaceutically acceptable salt thereof, comprising identifying whether one or more decreases in mutant allele frequencies are observed in the patient's blood, selecting the patient if said decreases are observed, and administering to the selected patient a therapeutically effective amount of H3B-6545 or a pharmaceutically acceptable salt thereof. Mutant allele frequency is the relative frequency of an mutant allele (variant of a gene) at a particular locus in a population, expressed as a fraction or percentage.

H3B-6545 is reported in U.S. Pat. No. 9,796,683 B2, which is incorporated by reference herein.

In some embodiments as reported herein, the pharmaceutically acceptable salt of H3B-6545 is an HCl salt of H3B-6545.

In some embodiments decreases in the mutant allele frequencies are observed in one or more alleles selected from the group consisting of PIK3CA, ESR1, TSC1, TP53, FGFR1, CCND1, ARID1A, POLE, FGF19, MET, NOTCH3, FGF3, AKT1, KRAS, MYC, ERBB2, ERBB3, FGFR3, PMS2, PTEN, RB1, BRAF, MDM2, ATR, ATRX, BRCA2, SETD2, ATM, FANCA, JAK2, NF1, SLX4, and SMAD4.

In a further embodiment decreases in mutant allele frequencies are observed in AKT1. In a further embodiment the AKT1 mutation location giving rise to the observed decrease in mutant allele frequency is E17. In a further embodiment the AKT1 mutation giving rise to the observed decrease in mutant allele frequency is E17K.

In a further embodiment decreases in mutant allele frequencies are observed in ESR1. In a still further embodiment the ESR1 mutation location(s) giving rise to the observed decrease in mutant allele frequencies are selected from one or more members of the group consisting of E380, D538, L536, S463, and Y537. In a further embodiment the ESR1 mutation(s) giving rise to the observed decrease in mutant allele frequencies are selected from one or more members of the group consisting of E380Q, D538G, L536H, L536P, L536R, S463P, Y537C, Y537N, and Y537S. In a further embodiment the ESR1 mutation giving rise to the observed decrease in mutant allele frequency is S463P. In a further embodiment the ESR1 mutation giving rise to the observed decrease in mutant allele frequency is Y537N.

In a further embodiment the decreases in mutant allele frequencies are observed in PIK3CA. In a further embodiment the PIK3CA mutation location(s) giving rise to the observed decreases in mutant allele frequencies are selected from one or more members of the group consisting of E542, E545 and H1047. In a further embodiment the PIK3CA mutation(s) giving rise to the observed decreases in mutant allele frequencies are selected from one or more members of the group consisting of E542K, E545K, H1047L and H1047R.

Further embodiments may provide a method of discontinuing treatment with compound H3B-6545 or a pharmaceutically acceptable salt thereof from a patient undergoing treatment with compound H3B-6545:

(H3B-6545)

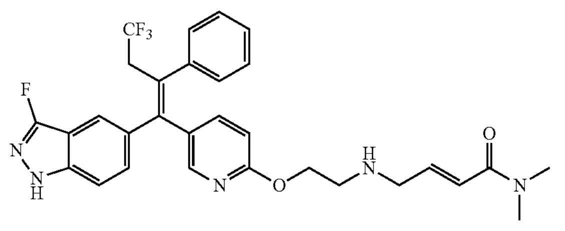

or a pharmaceutically acceptable salt thereof, comprising identifying whether one or more increases in mutant allele frequencies are observed in the patient's blood, and discontinuing treatment from the patient if said increases are observed.

In some embodiments increases in mutant allele frequencies are observed in one or more alleles selected from PIK3CA, ESR1, TSC1, TP53, FGFR1, CCND1, ARID1A, POLE, FGF19, MET, NOTCH3, FGF3, AKT1, KRAS, MYC, ERBB2, ERBB3, FGFR3, PMS2, PTEN, RB1, BRAF, MDM2, ATR, ATRX, BRCA2, SETD2, ATM, FANCA, JAK2, NF1, SLX4, and SMAD4.

In some embodiments increases in mutant allele frequencies are observed in ESR1. In yet still further embodiments, ESR1 mutation locations giving rise to the observed increase in said mutant allele frequencies are selected from one or more members of the group consisting of E380, D538, L536, S463, and Y537. In further embodiments, ESR1 mutation(s) giving rise to the observed increase of said mutant allele frequencies are selected from at least one member the group consisting of E380Q, D538G, L536H, L536P, L536R, S463P, Y537C, Y537N, and Y537S.

In further embodiments, increases in mutant allele frequencies are observed in PIK3CA. In still further embodiments PIK3CA mutation location(s) giving rise to said observed increases in mutant allele frequencies are selected from the group consisting of E542, E545 and H1047. In yet still further embodiments, mutations of PIK3CA giving rise to the observed increases in said mutant allele frequencies are selected from the group consisting of E542K, E545K, H1047L and H1047R. In further embodiments the PIK3CA mutation is E545K.

In a further embodiment increases in mutant allele frequencies are observed in AKT1. In a further embodiment the AKT1 mutation location giving rise to the observed increase in mutant allele frequency is E17. In further embodiments the AKT1 mutation giving rise to the observed increase in mutant allele frequency is E17K.

In still further embodiments, an identifying step occurs after the patient has received at least one treatment with compound H3B-6545:

(H3B-6545)

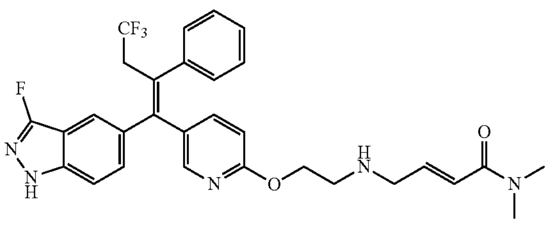

or a pharmaceutically acceptable salt thereof.

In further embodiments said patient has breast cancer. In still further embodiments said breast cancer is an estrogen receptor alpha (ERα) positive breast cancer. In yet still further embodiments said ERα has a mutation.

In still further embodiments increases in mutant allele frequencies are observed in circulating tumor DNA. In further embodiments decreases in mutant allele frequencies are observed in circulating tumor DNA.

Documents reported herein are incorporated by reference. If those documents conflict with this document, then this document controls.

BRIEF DESCRIPTION OF THE FIGURES

FIG. 5A to 5E show BEAMing assay. A. Baseline ESR1 and PIK3CA mutation status of patients; B and C. Clonalities of ESR1 and PIK3CA mutations; D and E. Amino acid distribution of PIK3CA and ESR1 mutations.

FIG. 6A shows allele frequency distribution and concordance of tissue and liquid biopsy mutations. FIG. 6B is a summary table of tissue and liquid biopsy mutation concordance.

FIG. 8A shows ratio of AF baseline/C2D1 with each patient colored separately. One patient may have multiple mutations. FIG. 7B and FIG. 7C show example ctDNA dynamics in a patient with progressive disease (B) vs partial response (C).

DETAILED DESCRIPTION

Definitions

Figure 1:
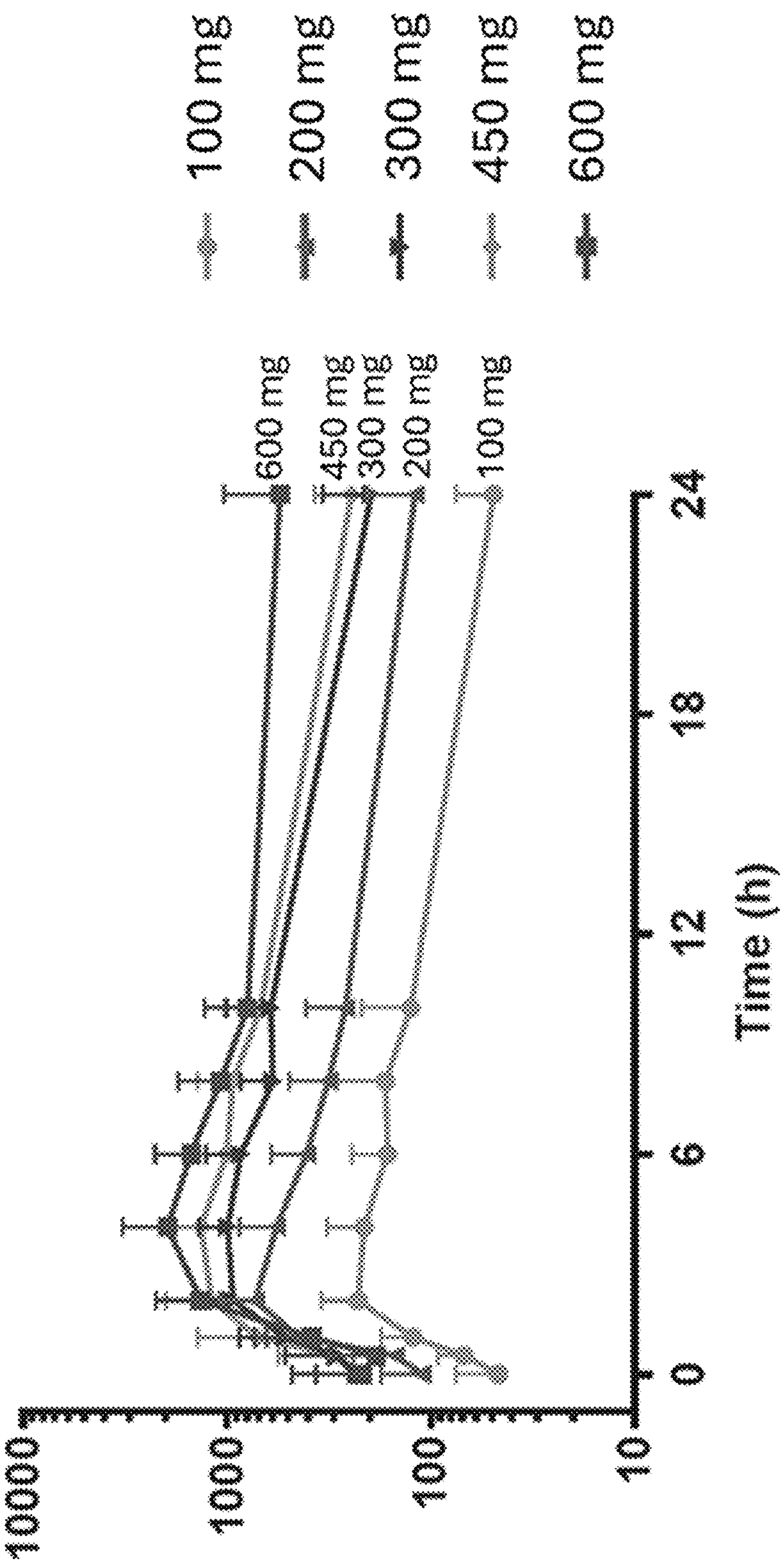
FIG. 1 shows a mean plasma-concentration over time profile for H3B-6545 (Cycle 1, Day 1) in Example 3. Preliminary PK analyses indicate that H3B-6545 exhibited a roughly dose-proportional increase in plasma exposure from 100 mg to 600 mg. The $t_{max}$ and half-life appeared independent of dose and time.

The use of the articles "a," "an," and "the" herein are to be construed to cover both the singular and the plural, unless otherwise indicated herein or clearly contradicted by context. For example, the term "a disintegrant" refers to one or more disintegrants included in or suitable for use in the formulation described herein. Similarly, the term "a therapeutic amount" refers to one or more therapeutic amounts included in or suitable for use in the dosage form.

The terms "comprising," "having," "including," and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The expression "bioequivalent" or "bioequivalence" is a term of art and is intended to be defined in accordance with Approved Drug Products with Therapeutic Equivalence Evaluations, 34th Edition, which is published by the U.S Department of Health and Human Services, and is commonly known as the "Orange Book." Bioequivalence of different formulation of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. Detailed guidelines for establishing the bioequivalence of a formulation with a reference formulation have been published by the FDA Office of Generic Drugs, Division of Bioequivalence.

As used herein, the term "a mean" refers to a geometric mean determined from a collection of independent measurements. For example, the independent measurements may be collected from a statistically meaningful population. As further examples, when used to describe pharmacokinetic parameters (such as "a mean $C_{max}$", "a mean $AUC_{0-x}$", "a mean $AUC_{0-t}$", "a mean $AUC_{0-inf}$", a "mean $t_{max}$", or "a mean $t_{1/2}$" (or "a mean half-life")), "a mean" refers to the geometric mean pharmacokinetic value derived from the population from which individual measurements were respectively collected. Hence, as used herein, a dosage form may be administered to a human subject, wherein the dosage form has a mean pharmacokinetic value derived from a collection of independently measured values.

The list of the abbreviations and definitions of the terms used in this application is as follows. AUC: Area under the plasma concentration-time curve; $AUC_{0-x}$: Area under the plasma concentration-time curve from time zero to x hours after dosing (e.g., x may indicate 12 or 24 hours); $AUC_{0-t}$: Area under the plasma concentration-time curve from time zero to time of last quantifiable concentration; $AUC_{0-inf}$: Area under the plasma concentration-time curve from time zero to infinity; ANCOVA: Analysis of covariance; CI: Confidence interval; $C_{max}$: Maximum drug concentration; $C_x$: plasma concentration at x hours after dosing; CV: Coefficient of variation; LC-MS/MS: Liquid chromatography-mass spectrometry/mass spectrometry; MAD: Multiple ascending dose; MTD: Maximum tolerated dose; PD: Pharmacodynamics; PK pharmacokinetic(s); RT: Reaction time; SAD: Single ascending dose; SD: Standard deviation; $t_{1/2}$: terminal elimination half-life; $t_{max}$: time to reach maximum (peak) concentration following drug administration. As used herein, $t_{1/2}$ includes the terminal elimination half-life of the drug concentration, which may be the terminal elimination half-life of the $C_{max}$. As used herein, $C_{max}$ includes the maximum drug concentration of a substance as measured in human plasma.

Two dosage forms whose rate and extent of absorption differ by −20%/+25% or less are generally considered "bioequivalent". Another approach for average bioequivalence involves the calculation of a 90% confidence interval for the ratio of the averages (population geometric means) of the measures for the test and reference products. To establish BE, the calculated confidence interval should fall within usually 80-125% for the ratio of the product averages. In addition to this general approach, the others approach, including (1) logarithmic transformation of pharmacokinetic data, (2) methods to evaluate sequence effects and (3) methods to evaluate outlier data, may be useful for the establishment of bioequivalence. For example, in the above (1) the confidence interval should fall within usually 80-125% for the difference in the mean value of the logarithmic converted PK parameter.

The term "about," "approximately," or "approximate," as used herein when referring to a measureable value such as an amount, a temporal duration, and the like, is meant to encompass variations of ±20% or 10%, more preferably 5%, even more preferably 1%, and still more preferably 0.1% from the specified value, as such variations are appropriate in the given context.

When a dosage amount or dosage range is mentioned by mass or weight in the format of "Compound of Formula I," or "H3B-6545," or "free base of H3B-6545," a person of skill in the art will appreciate that providing the equivalent molar amount of the active compound as a pharmaceutically acceptable salt will typically require administration of a larger mass of salt than would be required through administration of the compound alone (that is, the amount of free base and amount of salt have a 1:1 molar ratio). For example, the phrase "25 mg to 50 mg of a compound given by Formula I or a pharmaceutically acceptable salt thereof" contemplates the free base of Formula I in amounts from 25 mg to 50 mg (inclusive of endpoints), as well as the monohydrochloride salt of a compound of Formula I in amounts 26 mg to 53 mg (inclusive of endpoints). This conversion may be referred to, for example, as a "salt conversion factor," "salt correction factor," or "potency adjustment factor."

The potency adjustment factor conversion is also applicable to crystalline forms of Formula I existing as a hydrate, solvate, or crystalline forms of Formula I having both i) hydrate or solvate and ii) salt counterions. Moreover, such potency adjustment factor conversions are applicable whether co-crystallized solvent molecules and/or salt counterions exist in the crystalline form in integral or non-integral stoichiometric ratios. Hence, the skilled artisan understands that different potency adjustments may be made for the monohydrochloride salt of H3B-6545, the hemi-hydrochloride salt of H3B-6545, or unusual ratios such 1:1.3, 1:1.25, etc.

Consistent with the prior paragraphs above, as used herein, an "equivalent" quantity (e.g., mass, weight, dosage, etc.) of Formula I (or H3B-6545, free base of H3B-6545 or any other of its synonyms as used herein) refers to the quantity of any salt and/or hydrate following its potency adjustment factor.

"H3B-6545 drug substance" refers to a monohydrochloride salt of H3B-6545, as reported in U.S. Pat. No. 10,640,483, which is incorporated by reference herein.

As used herein, a "human subject" is interchangeable with a "human subject in need of treatment," or "human subject in need thereof," all of which refer to a human subject having breast cancer, or a human subject having an increased risk of developing breast cancer relative to the population at large. A human subject in need thereof can be one who has been previously diagnosed or identified as having breast cancer or a precancerous condition. Alternatively, a human subject in need thereof can be one who has an increased risk of developing such disorder relative to the population at large (i.e., a subject who is predisposed to developing such disorder relative to the population at large). A human subject in need thereof can have a precancerous condition.

A human subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition.

As used herein, "fasted condition" describes a human subject in need thereof who has undergone an overnight fast of at least 10 hours before administration. No food should be allowed for at least 4 hours post-dose. Water can be allowed as desired except for one hour before and after drug administration.

As used herein, "fed state" describes that following an overnight fast of at least 10 hours, a human subject who ate a high-fat breakfast in 30 minutes or less and then took a single dose of H3B-6545 within 30 minutes after the start of the meal. Water was allowed as desired except for one hour before and after drug administration.

As used herein, "treating" or "treat" describes the management and care of a human subject for the purpose of combating a disease, condition, or disorder and includes the administration of a dosage form of H3B-6545, or a pharmaceutically acceptable salt, polymorph, hydrate or solvate thereof, to alleviate the symptoms or complications of a disease, condition or disorder, or to eliminate the disease, condition or disorder.

H3B-6545, or a pharmaceutically acceptable salt and/or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

As used herein, "sample" means any biological sample derived from the human subject which includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, the term "dosage form" refers to physically discrete units suited as unitary dosages for a human subject to be treated; each unit containing a predetermined quantity of active compound calculated to produce the desired therapeutic effect in association with the required pharmaceutical carrier. Dosage forms are classified in terms of administration routes and application sites, including, for example, oral, topical, rectal, vaginal, intravenous, subcutaneous, intramuscular, ophthalmic, nasal, optic and inhalation administration. Alternatively, dosage forms are classified in terms of physical form such as solid, semi-solid or liquid. The dosage form is any of a variety of forms, including, for example, an IV bag, a tablet, a single pump on an aerosol inhaler or a vial. An "oral dosage form" refers to a dosage form that is easily administered to a human subject through the mouth. Non-limiting examples of oral dosage forms include capsules and tablets. The quantity of active ingredient (e.g., a formulation of the disclosed compound or salt, hydrate, or solvate thereof) in a unit dose is an effective amount and is varied according to the particular treatment involved.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. For example, a pharmaceutically acceptable excipient used for the formulation of the invention can be a diluent or inert carrier, a lubricant, a binder, or a combination thereof. The pharmaceutically acceptable excipient used for the formulation of the invention can further include a filler, an anti-microbial agent, an antioxidant, an anti-caking agent, a coating agent, or a mixture thereof.

The term "composition" as used herein includes a product comprising a particular ingredient in a particular amount and any product directly or indirectly brought about by the combination of particular ingredients in particular amounts. Such a term as it relates to pharmaceutical compositions is intended to include a product comprising an active ingredient (here, Formula I or any of its pharmaceutically acceptable salts, hydrates and/or solvates) and an inert ingredient constituting a carrier and include any product directly or indirectly brought about by the combination, complexation or aggregation of any two or more ingredients or the dissociation, other kinds of reactions or interaction of one or more ingredients. Thus, the pharmaceutical composition of the present invention includes any composition prepared by mixing compounds given by Formula I (or pharmaceutically acceptable salts, hydrates and/or solvates) with a pharmaceutically acceptable excipient.

As used herein, the term "therapeutically effective amount" refers to an amount of H3B-6545 that can produce a therapeutic effect in a human subject. A therapeutically effective amount is an amount that can treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician.

In a preferred aspect, the disease or condition to be treated is cancer. In another aspect, the disease or condition to be treated is a cell proliferative disorder. The therapeutically effective amount of H3B-6545 may be administered in a dosage form. A therapeutically effective amount H3B-6545 may be in the form of a pharmaceutically acceptable salt, solvate, and/or hydrate.

As used herein, "therapeutic effect" is a consequence of a medical treatment of any kind, the results of which are judged to be desirable and beneficial. This is true whether the result was expected, unexpected, or even an unintended consequence of the treatment. A desirable or beneficial result may be the inhibition of altered cell signaling pathways, inhibition of cell growth, preferably cancer cell growth, promotion of cell death, preferably cancer cell death, or the shrinkage of tumors, all of which are observed without severe adverse effects. Slowing, and preferably regressing, the growth of the tumors and also preferably causing complete regression of a cancer is another example of a therapeutic effect. A therapeutic effect may also be an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped.

Severe adverse effects may include those that are life threatening (such as liver failure, abnormal heart rhythms, and certain types of allergic reactions), those that result in persistent or significant disability or hospitalization, or those that cause a birth defect.

As used herein, "pharmaceutically acceptable salts" refer to derivatives of H3B-6545 wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

As used herein, "quantifiable" means being able to be measured, calculated or expressed as a quantity or numerical value. A quantifiable plasma concentration is a concentration of H3B-6545 that is able to be detected and measured within the plasma of a human subject after administration. A quantifiable AUC bioavailability is a fraction of H3B-6545 that gains access to the systemic circulation of a human subject that is able to be calculated from analyzing H3B-6545's plasma concentrations in plasma samples taken from a human subject over a set period of time. A quantifiable half-life is a detectable or calculated time wherein the plasma concentration of H3B-6545 is 50% of the maximum quantifiable plasma concentration of H3B-6545. The methods and materials needed to quantify the aforementioned PK parameters are commonly known to those of ordinary skill in the art. Specific quantification methods are presented within the present application.

As used herein, the term "solvate" means solvent addition forms that contain either stoichiometric or non-stoichiometric amounts of solvent.

As used herein, the term "tautomer" means one of two or more structural isomers that exist in equilibrium and is readily converted from one isomeric form to another.

Unless specifically stated or obvious from context, as used herein, the term "or" is understood to be inclusive.

An aspect of the present invention provides a dosage form with a therapeutically effective amount of H3B-6545, or a pharmaceutically acceptable salt thereof, and at least one pharmaceutically acceptable carrier or excipient which can be administered to a human subject in need thereof, wherein the therapeutically effective amount achieves a quantifiable plasma concentration after administration. In an embodiment of the invention, the dosage form is an oral dosage form. In another embodiment of the invention, the dosage form is solid dosage form. In another embodiment of the invention, the dosage form is a solid oral dosage form. In yet another embodiment, the solid oral dosage form may be an immediate release oral solid dosage form. The oral solid dosage form may be in the form of a tablet or capsule. These forms may have multiple phases, including, for example, an internal phase and an external phase.

In one embodiment, the dosage form is substantially free of water. In this context, "substantially" free of water means that the water content of the formulation at the time of packaging is less than 7%, less than 5%, less than 1%, or less than 0.5% of the total weight of the formulation. In one embodiment the amount of water is between 0.1 to 5% (e.g., 0.1-1% or 0.1-0.5%) of the total weight of the formulation. In one embodiment, the amount of water in the formulation of the invention manufactured through a spray-coating process is less than 0.5%.

The at least one pharmaceutically acceptable excipient may be a diluent or inert carrier, a disintegrant, a lubricant, a binder, or a combination thereof. The pharmaceutically acceptable excipient may also include a filler, an anti-microbial agent, an antioxidant, an anti-caking agent, a coating agent, or a mixture thereof.

Exemplary binders may include, but are not limited to corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc.), methyl cellulose, methocel, pre-gelatinized starch (e.g., STARCH 1500® and STARCH 1500 LM®, sold by Colorcon, Ltd.), hydroxypropyl cellulose, hydroxypropyl methyl cellulose, microcrystalline cellulose (FMC Corporation, Marcus Hook, PA, USA), Emdex, Plasdone, or mixtures thereof; fillers, such as talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof.

Exemplary disintegrants may include, but are not limited to: agar-agar, alginic acid, calcium carbonate, microcrystalline cellulose, croscarmellose sodium, crospovidone, polacrilin potassium, sodium starch glycolate (such as Explotab), potato or tapioca starch, other starches, pre-gelatinized starch, clays, other algins, other celluloses, gums (like gellan), low-substituted hydroxypropyl cellulose, ployplasdone, or mixtures thereof.

Exemplary lubricants may include, but are not limited to: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R Grace Co., Baltimore, MD USA), a coagulated aerosol of synthetic silica (Deaussa Co., Piano, TX USA), a pyrogenic silicon dioxide (CAB-O-SIL, Cabot Co., Boston, MA USA), or mixtures thereof.

Exemplary coating agents may include, but are not limited to: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, camauba wax, microcrystalline wax, gellan gum, maltodextrin, methacrylates, microcrystalline cellulose and carrageenan or mixtures thereof.

In one embodiment, the dosage form is a solid oral dosage form that may optionally be treated with coating systems (e.g. Opadry® fx film coating system) to be coated with for example Opadry® blue (OY-LS-20921), Opadry® white (YS-2-7063), Opadry® white (YS-1-7040), and black ink (S-1-8 106).

In one embodiment, the oral dosage form is configured into a capsule that possesses an internal phase that comprises a therapeutically effective amount of H3B-6545 or a pharmaceutically acceptable salt thereof, lactose monohydrate, low-substituted hydroxypropyl cellulose, microcrystalline cellulose, hydroxypropylcellulose and colloidal anhydrous silica. The capsule also possesses an external phase comprising magnesium stearate.

In one embodiment, the capsule is hypromellose.

In another embodiment, the capsule is hypromellose and is further comprised of iron oxide red and titanium dioxide.

In another embodiment, the oral dosage form is a capsule that comprises by total weight of the capsule 25% to 30% a therapeutically effective amount of H3B-6545, or a pharmaceutically acceptable salt, 10% to 15% lactose monohydrate, 5% to 10% low-substituted hydroxypropyl cellulose, 1% to 5% microcrystalline cellulose, 0.5% to 5% hydroxypropylcellulose, 0.05% to 0.5% colloidal anhydrous silica, 0.1% to 1% magnesium stearate, 40% to 45% hypromellose, 0.5% to 2% iron oxide red and 0.5% to 2% titanium dioxide.

The pharmaceutically acceptable salt may include conventional non-toxic salts or the quintenary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts may include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

In another embodiment, the dosage form may also comprise one or more active compounds (e.g., H3B-6545 or a salt thereof) in combination with at least one pharmaceutically acceptable excipient or carrier.

Examples of solvates may include, if the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

The oral dosage form with a therapeutically effective amount of H3B-6545, or a pharmaceutically acceptable salt thereof, and at least one pharmaceutically acceptable carrier or excipient which can be administered to a human subject in need thereof may achieve a quantifiable plasma concentration from about 0.5 hr to about 12 hr, from about 0.5 hr to about 5 hr, from about 0.5 hr to about 3 hr, from about 1 hr to about 5 hrs or from about 1 hr to about 3 hr after administration.

A therapeutically effective amount of H3B-6545, or a pharmaceutically acceptable salt thereof, that may be present within the oral dosage form ranges from about 50 mg to about 1000 mg, from about 100 mg to about 800 mg, from about 100 mg to about 600 mg, from about 200 mg to about 600 mg or from about 400 mg to about 600 mg.

In a preferred embodiment, the therapeutically effective amount of H3B-6545, or a pharmaceutically acceptable salt thereof that may be present within the oral dosage is 450 mg. In an embodiment of the invention, these aforementioned dosages are daily dosages.

The oral dosage form with a therapeutically effective amount of H3B-6545, or a pharmaceutically acceptable salt thereof, and at least one pharmaceutically acceptable carrier or excipient which can be administered to a human subject in need thereof may achieve a maximum quantifiable plasma concentration from about 170 ng/mL to about 2000 ng/mL, from about 200 ng/mL to about 1500 ng/mL, from about 500 ng/mL to about 2000 ng/mL, from about 500 ng/mL to about 1500 ng mL, from about 1000 ng/mL to about 2000 ng/mL or from about 1000 ng/mL to about 1500 ng/mL after administration.

The oral dosage form with a therapeutically effective amount of H3B-6545, or a pharmaceutically acceptable salt thereof, and at least one pharmaceutically acceptable carrier or excipient which can be administered to a human subject in need thereof may achieve a half-life from about 5 hr to about 24 hr, from about 8 hr to about 24 hr, from about 8 hr to about 15 hr, from about 10 hr to about 15 hr or from about 15 hr to about 24 hr after administration.

The oral dosage form with a therapeutically effective amount of H3B-6545, or a pharmaceutically acceptable salt thereof, and at least one pharmaceutically acceptable carrier or excipient which can be administered to a human subject in need thereof may achieve a quantifiable AUC bioavailability from about 2,000 ng*hr/mL to about 20,000 ng*hr/mL, from about 5,000 ng*hr/mL to about 20,000 ng*hr/mL, from about 10,000 ng*hr/mL to about 20,000 ng*hr/mL, from about 15,000 ng*hr/mL to about 20,000 ng*hr/mL, from about 5,000 ng*hr/mL to about 15,000 ng*hr/mL or from about 10,000 ng*hr/mL to about 15,000 ng*hr/mL after administration.

The oral dosage form with a therapeutically effective amount of H3B-6545, or a pharmaceutically acceptable salt thereof, and at least one pharmaceutically acceptable carrier or excipient which can be administered to a human subject in need thereof may be administered orally as a single dose once per day during a 20-day cycle, a 21-day cycle, a 22-day cycle, a 23-day cycle, a 24-day cycle, a 25-day cycle, a 26-day cycle, a 27-day cycle, a 28-day cycle or until a therapeutic effect occurs within the subject in need thereof. The dosage form may also be administered in cycles under 20 days.

A. Oral Dosage Forms Comprising from about 100 mg to about 600 mg of H3B-6545, or a Pharmaceutically Acceptable Salt Thereof, and at Least One Pharmaceutically Acceptable Excipient.

In some embodiments, an oral dosage form comprises from about 100 mg to about 600 mg of H3B-6545, or a pharmaceutically acceptable salt thereof, and at least one pharmaceutically acceptable excipient. In such embodiments the dosage achieves a maximum quantifiable plasma concentration, Cmax (in ng/mL), following administration to a subject in need of treatment of from about 150 ng/mL to about 2100 ng/mL. In other embodiments the dosage achieves a maximum quantifiable plasma concentration following administration to a subject in need of treatment of from about 250 ng/mL to about 1700 ng/mL. In further embodiments the dosage achieves a maximum quantifiable plasma concentration following administration to a subject in need of treatment of from about 1200 ng/mL to about 1500 ng/mL. In these embodiments the stated Cmax may be achieved in a time between about 1 hours to about 25 hours; about 2 hours to about 12 hours; about 2 hours to about 5 hours; or about 4 hours.

In one embodiment, the oral dosage form comprises from about 100 to 600 mg of H3B-6545, or a pharmaceutically acceptable salt thereof, and at least one pharmaceutically acceptable excipient. In such an embodiment the oral dosage form is able to achieve a Cmax range of about 1.8 ng/mL to about 4.0 ng/mL per mg of H3B-6545. In a further embodiment the oral dosage form is able achieve a Cmax range of about 1.8 ng/mL to about 3.4 ng/mL per mg of H3B-6545. In a still further embodiment the oral dosage form is able to achieve a Cmax range of about 3.0 ng/mL to about 4.0 ng/mL per mg of H3B-6545.

In some embodiment, the oral dosage form comprises from about 100 mg to about 600 mg of H3B-6545, or a pharmaceutically acceptable salt thereof, and at least one pharmaceutically acceptable excipient. In some of those embodiments the dosage form achieves a half-life after administration to a human subject in need thereof of from about 8.0 hours to about 22.0 hours; or a half-life of about 10.0 hours to about 13.0 hours.

In one embodiment, the oral dosage form comprises from about 100 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-24 hours) after administration to a human subject in need thereof of from about 1,600 ng*hr/mL to about 23,000 ng*hr/mL; about 2,500 ng*hr/mL to about 18,500 ng*hr/mL; about 4,000 ng*hr/mL to about 20,000 ng*hr/mL; or about 9,000 ng*hr/mL to about 17,000 ng*hr/mL.

In one embodiment the oral dosage form comprises from about 100 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-24 hours) after administration to a human subject in need thereof, as measured on the basis of "per milligram of H3B-6545," of about 17 ng*hr/mL/mg to about 40 ng*hr/mL/mg; about 17 ng*hr/mL/mg to about 37 ng*hr/mL/mg, or about 26 ng*hr/mL/mg to about 40 ng*hr/mL/mg.

In one embodiment, the oral dosage form comprises from about 100 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-infinity hours) after administration to a human subject in need thereof of from about 2,000 ng*hr/mL to about 40,000 ng*hr/mL; about 5,000 ng*hr/mL to about 25,000 ng*hr/mL, or about 20,000 ng*hr/mL to about 23,000 ng*hr/mL.

In one embodiment the oral dosage form comprises from about 100 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-infinity) after administration to a human subject in need thereof, as measured on the basis of "per milligram of H3B-6545," of about 21 ng*hr/mL/mg to about 66 ng*hr/mL/mg; about 21 ng*hr/mL/mg to about 55 ng*hr/mL/mg, or about 30 ng*hr/mL/mg to about 66 ng*hr/mL/mg.

B. Oral Dosage Forms Comprising from about 300 mg to about 600 mg of H3B-6545, or a Pharmaceutically Acceptable Salt Thereof, and at Least One Pharmaceutically Acceptable Excipient.

In some embodiments, an oral dosage form comprises from about 300 mg to about 600 mg of H3B-6545, or a pharmaceutically acceptable salt thereof, and at least one pharmaceutically acceptable excipient. In such embodiments the dosage achieves a maximum quantifiable plasma concentration, Cmax (in ng/mL), following administration to a subject in need of treatment of from about 900 ng/mL to about 2100 ng/mL. In other embodiments the dosage achieves a maximum quantifiable plasma concentration following administration to a subject in need of treatment of from about 1100 ng/mL to about 1900 ng/mL. In further embodiments the dosage achieves a maximum quantifiable plasma concentration following administration to a subject in need of treatment of from about 1200 ng/mL to about 1700 ng/mL. In these embodiments the stated Cmax may be achieved in a time between about 1 hours to about 25 hours; about 2 hours to about 10 hours; about 2 hours to about 5 hours; or about 4 hours.

In one embodiment, the oral dosage form comprises from about 300 to 600 mg of H3B-6545, or a pharmaceutically acceptable salt thereof, and at least one pharmaceutically acceptable excipient. In such an embodiment the oral dosage form is able to achieve a Cmax range of about 3.0 ng/mL to about 4.0 ng/mL per mg of H3B-6545. In a further embodiment the oral dosage form is able achieve a Cmax range of about 3.0 ng/mL to about 3.4 ng/mL per mg of H3B-6545.

In some embodiment, the oral dosage form comprises from about 300 mg to about 600 mg of H3B-6545, or a pharmaceutically acceptable salt thereof, and at least one pharmaceutically acceptable excipient. In some of those embodiments the dosage form achieves a half-life after administration to a human subject in need thereof of from about 9.5 hours to about 14.5 hours; or a half-life of about 10.0 hours to about 11.0 hours.

In one embodiment, the oral dosage form comprises from about 300 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-24 hours) after administration to a human subject in need thereof of from about 9,000 ng*hr/mL to about 23,000 ng*hr/mL or about 12,000 ng*hr/mL to about 19,000 ng*hr/mL.

In one embodiment the oral dosage form comprises from about 300 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-24 hours) after administration to a human subject in need thereof, as measured on the basis of "per milligram of H3B-6545," of about 30 ng*hr/mL/mg to about 40 ng*hr/mL/mg or about 30 ng*hr/mL/mg to about 37 ng*hr/mL/mg.

In one embodiment, the oral dosage form comprises from about 300 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-infinity hours) after administration to a human subject in need thereof of from about 11,000 ng*hr/mL to about 40,000 ng*hr/mL; about 11,000 ng*hr/mL to about 33,000 ng*hr/mL, or about 12,000 ng*hr/mL to about 40,000 ng*hr/mL.

In one embodiment the oral dosage form comprises from about 300 mg to about 600 mg of H3B-6545, or a pharmaceutically acceptable salt thereof, and at least one pharmaceutically acceptable excipient. In such an embodiment the dosage may achieve a quantifiable AUC bioavailability (from 0-infinity) after administration to a human subject in need thereof, as measured on the basis of "per milligram of H3B-6545," of about 37 ng*hr/mL/mg to about 66 ng*hr/mL/mg; about 37 ng*hr/mL/mg to about 54 ng*hr/mL/mg, or about 38 ng*hr/mL/mg to about 66 ng*hr/mL/mg.

C. Oral Dosage Forms Comprising about 450 mg of H3B-6545, or a Pharmaceutically Acceptable Salt Thereof, and at Least One Pharmaceutically Acceptable Excipient.

In some embodiments, an oral dosage form comprises about 450 mg of H3B-6545, or a pharmaceutically acceptable salt thereof, and at least one pharmaceutically acceptable excipient. In such embodiments the dosage achieves a maximum quantifiable plasma concentration, Cmax (in ng/mL), following administration to a subject in need of treatment of from about 1,000 ng/mL to about 1,600 ng/mL. In other embodiments the dosage achieves a maximum quantifiable plasma concentration following administration to a subject in need of treatment of from about 1,100 ng/mL to about 1,500 ng/mL. In further embodiments the dosage achieves a maximum quantifiable plasma concentration following administration to a subject in need of treatment of from about 1,200 ng/mL to about 1,400 ng/mL. In these embodiments the stated Cmax may be achieved in a time between about 3 hours to about 6 hours or about 4 hours to about 6 hours.

In one embodiment, the oral dosage form comprises about 450 mg of H3B-6545, or a pharmaceutically acceptable salt thereof, and at least one pharmaceutically acceptable excipient. In such an embodiment the oral dosage form is able to achieve a Cmax range of about 2.4 ng/mL to about 3.5 ng/mL per mg of H3B-6545. In a further embodiment the oral dosage form is able achieve a Cmax range of about 3.0 ng/mL to about 3.5 ng/mL per mg of H3B-6545. In a still further embodiment the oral dosage form is able to achieve a Cmax range of about 3.3 ng/mL to about 3.5 ng/mL per mg of H3B-6545.

In some embodiment, the oral dosage form comprises about 450 mg of H3B-6545, or a pharmaceutically acceptable salt thereof, and at least one pharmaceutically acceptable excipient. In some of those embodiments the dosage form achieves a half-life after administration to a human subject in need thereof of from about 8.0 hours to about 11.0 hours; or a half-life of about 9.0 hours to about 10.0 hours.

In one embodiment, the oral dosage form comprises about 450 mg of H3B-6545, or a pharmaceutically acceptable salt thereof, and at least one pharmaceutically acceptable excipient. In such an embodiment the dosage may achieve a quantifiable AUC bioavailability (from 0-24 hours) after administration to a human subject in need thereof of from about 12,000 ng*hr/mL to about 20,000 ng*hr/mL; about 14,000 ng*hr/mL to about 16,000 ng*hr/mL, or about 12,000 ng*hr/mL to about 17,000 ng*hr/mL.

In one embodiment the oral dosage form comprises about 450 mg of H3B-6545, or a pharmaceutically acceptable salt thereof, and at least one pharmaceutically acceptable excipient. In such an embodiment the dosage may achieve a quantifiable AUC bioavailability (from 0-24 hours) after administration to a human subject in need thereof, as measured on the basis of "per milligram of H3B-6545," of about 27 ng*hr/mL/mg to about 43 ng*hr/mL/mg; about 30 ng*hr/mL/mg to about 40 ng*hr/mL/mg, or about 30 ng*hr/mL/mg to about 35 ng*hr/mL/mg.

In one embodiment, the oral dosage form comprises about 450 mg of H3B-6545, or a pharmaceutically acceptable salt thereof, and at least one pharmaceutically acceptable excipient. In such an embodiment the dosage may achieve a quantifiable AUC bioavailability (from 0-infinity hours) after administration to a human subject in need thereof of from about 16,000 ng*hr/mL to about 26,000 ng*hr/mL; about 16,000 ng*hr/mL to about 23,000 ng*hr/mL, or about 16,000 ng*hr/mL to about 18,000 ng*hr/mL.

In one embodiment the oral dosage form comprises about 450 mg of H3B-6545, or a pharmaceutically acceptable salt thereof, and at least one pharmaceutically acceptable excipient. In such an embodiment the dosage may achieve a quantifiable AUC bioavailability (from 0-infinity) after administration to a human subject in need thereof, as measured on the basis of "per milligram of H3B-6545," of about 36 ng*hr/mL/mg to about 57 ng*hr/mL/mg; about 38 ng*hr/mL/mg to about 52 ng*hr/mL/mg, or about 35 ng*hr/mL/mg to about 40 ng*hr/mL/mg.

Embodiments may also relate to a method for treating breast cancers (i.e., those that are ERα-positive and/or HER2 negative), wherein the method comprises administering to a human subject in need thereof any oral dosage form described herein to obtain the PK results that are described.

In all embodiments pertaining to the method of treatment, the human subject in need thereof may be in a fed or fasted condition.

Nonclinical findings support dose dependent inhibition of ERαWT and ERαmut-dependent transcription and a subsequent decrease in cell proliferation. Safety, pharmacokinetics (PK), and pharmacodynamics (PD) of H3B-6545 in women with ER+, HER2-negative breast cancer (BC) are considered to identify a recommended phase 2 dose (RP2D).

ESR1 gene constitutively activating mutations, found in ~30% of MBC tumors, are located within the ligand-binding domain, and can confer resistance to estrogen deprivation therapy (e.g., aromatase inhibition) and promote resistance to anti-ER therapies. Li S., et al. *Cell Reports,* 2013; 4:1116-1130; Robinson DR, Wu YM, Vats P, et al. *Nature genetics,* 2013; 45:1446-1451; Toy W, Shen Y, Won H, et al. *Nature genetics.* 2013; 45:1439-1445.

H3B-6545 is an orally available selective ER covalent antagonist that inhibits both estrogen receptor α (ERα) mutant (MUT) and wild-type (WT) activity by irreversibly engaging with a unique cysteine not conserved in other nuclear hormone receptors. H3B-6545 potently suppresses ERα function without degrading the receptor.

Embodiments provide a method of treating a patient with H3B-6545 or a pharmaceutically acceptable salt thereof, comprising identifying whether one or more decreases in mutant allele frequencies are observed in the patient's blood, selecting the patient if said decreases are observed, and administering to the selected patient a therapeutically effective amount of H3B-6545 or a pharmaceutically acceptable salt thereof. Mutant allele frequency is the relative frequency of a mutant allele (variant of a gene) at a particular locus in a population, expressed as a fraction or percentage.

We report phase 1 dose escalation of H3B-6545, a first-in class highly Selective ERα Covalent Antagonist (SERCA), in women with ER-positive, HER2-negative breast cancer (HR+BC).

EXAMPLES

Example 1: Capsule Formulation

Example 1 reports formulation of capsules with various amounts of H3B-6545 drug substance. Capsules used in subsequent examples were made using this method. 25 mg, 50 mg and 150 mg strength capsules were formulated according to the following table:

TABLE 1

Components and Composition of H3B-6545 Capsules

| Component | Composition 25 mg Amount (mg) | Composition 50 mg Amount (mg) | Composition 150 mg Amount (mg) | Function | Specification |
|---|---|---|---|---|---|
| Internal Phase (Granules) | | | | | |
| H3B-6545 drug substance [a] (equivalent to free base) | 26.61 (25.0) | 53.22 (50.0) | 159.66 (150.0) | Active Ingredient | Not applicable |
| Lactose monohydrate [b] | 11.29 | 22.58 | 67.74 | Diluent | JP, NF, Ph. Eur. |
| Low-substituted hydroxypropyl cellulose | 7.5 | 15.0 | 45.0 | Disintegrant | JP, NF |
| Microcrystalline cellulose | 2.5 | 5.0 | 15.0 | Diluent | JP, NF, Ph. Eur. |
| Hydroxypropylcellulose | 1.5 | 3.0 | 9.0 | Binder | JP, NF, Ph. Eur. |
| Silica, colloidal anhydrous | 0.1 | 0.2 | 0.6 | Glidant | JP, NF, Ph. Eur. |
| Magnesium stearate | 0.25 | 0.5 | 1.5 | Lubricant | JP, NF, Ph. Eur. |
| External Phase (Granules) | | | | | |
| Magnesium stearate | 0.25 | 0.5 | 1.5 | Lubricant | JP, NF, Ph. Eur. |
| Total of capsule content | 50 | 100 | 300 | — | — |

TABLE 1-continued

| Components and Composition of H3B-6545 Capsules | | | | | |
|---|---|---|---|---|---|
| | Composition | | | | |
| Component | 25 mg | 50 mg Amount (mg) | 150 mg | Function | Specification |
| Capsule | | | | | |
| Hypromellose capsules [c] | 38 | 38 | 70 | Capsule shell | JP [d] |
| Total capsule weight | 88 | 138 | 370 | — | — |

NF = National Formulary (US),
Ph. Eur. = European Pharmacopoeia,
JP = Japanese Pharmacopoeia
[a] The quantity of H3B-6545 drug substance is adjusted as per potency adjustment factor, a derived value for the assay value in free form.
[b] Compounding amount of lactose monohydrate is adjusted depending on the quantity of H3B-6545 drug substance to maintain constant weight of powder.
[c] Components and composition of the Hypromellose capsules are provided in Tables 2 and 3.
[d] JP16 official monograph "Capsules" or JP17 official monograph "Hypromellose Capsules" is applied.

TABLE 2

| Components and Composition of Hypromellose Capsule Shell for H3B-6545 25 and 150 mg Capsules | | |
|---|---|---|
| Component | Specification | Composition (% w/w) |
| Iron oxide red | JPE, NF, EC Regulation (E172) | 1.1% |
| Titanium dioxide | JP, USP, Ph. Eur. | 0.6% |
| Hypromellose | JP, USP, Ph. Eur. | q.s. to 100% |

JPE = Japanese Pharmaceutical Excipients, NF = National Formulary(US), JP = Japanese Pharmacopoeia,
USP = United States Pharmacopeia, EC Regulation = European Commission Regulation, Ph.
Eur. = European Pharmacopoeia, q.s. = quantum sufficit. E172 is a European standard for iron oxide and hydroxides.

TABLE 3

| Components and Composition of Hypromellose Capsule Shell for H3B-6545 50 mg Capsules | | | |
|---|---|---|---|
| | | Composition (% w/w) | |
| Component | Specification | Cap | Body |
| Iron oxide red | JPE, NF, EC Regulation (E172) | 1.1% | — |
| Titanium dioxide | JP, USP, Ph. Eur. | 0.6% | 2.0% |
| Hypromellose | JP, USP, Ph. Eur. | q.s. to 100% | q.s. to 100% |

JPE = Japanese Pharmaceutical Excipients, NF = National Formulary (US), JP = Japanese Pharmacopoeia,
USP = United States Pharmacopeia, EC Regulation = European Commission Regulation, Ph.Eur. = European Pharmacopoeia, q.s. = quantum sufficit. E172 is a European standard for iron oxide and hydroxides.

In brief, capsules were made by forming an initial mixture of H3B-6545 drug substance, lactose monohydrate, low-substituted hydroxypropyl cellulose, microcrystalline cellulose, hydroxypropylcellulose and silica, colloidal anhydrous in a high shear mixer. Magnesium stearate was then mixed with the initial mixture using a high shear mixer. The resulting mixture was then compressed into ribbons using a roller compactor, passed through a screen (sizing), and mixed with magnesium stearate using a tumbler mixer. The final blends were filled into hypromellose capsules using an encapsulator.

Example 2: Tablet Formation

Example 2 reports formation of tables including H3B-6545 drug substance. Tablets discussed in subsequent examples were made using this method. H3B-6545 film-coated tablets containing 150 mg of H3B-6545 drug substance as free base were made according to the following formulation:

TABLE 4

| Composition of H3B-6545 Tablets | | | |
|---|---|---|---|
| Component | Specification | Function | mg/tablet |
| Core Tablet Internal phase | | | |
| H3B-6545 drug substance[a] (equivalent to free base) | Not applicable | Active ingredient | 159.6 (150.0) |
| Lactose monohydrate[b] | NF, Ph. Eur., JP | Diluent | 241.2 |
| Low-substituted hydroxypropyl cellulose | NF, JP | Disintegrant | 90.0 |
| Hypromellose | USP, Ph. Eur., JP | Binder | 18.0 |
| Colloidal silicon dioxide | NF, Ph. Eur., JP | Glidant | 1.2 |
| Purified water[c] | USP, Ph. Eur., JP | Solvent | q.s. |
| External phase | | | |
| Microcrystalline cellulose[d] | NF, Ph. Eur., JP | Diluent | 78.0 |
| Magnesium stearate[d] | NF, Ph. Eur., JP | Lubricant | 12.0 |
| Core tablet weight (mg) | — | — | 600.0 |
| Film-Coating | | | |
| OPADRY ® 03H420000 YELLOW[e] | NC | Coating agent | 30.0 |
| Purified water[f] | USP, Ph. Eur., JP | Solvent | q.s. |
| Total weight (mg) | — | — | 630.0 |

JP = Japanese Pharmacopoeia, NC = Non-compendial, NF = National Formulary (U.S.), Ph.
Eur. = European Pharmacopoeia, q.s. = quantum sufficit, USP = U.S. Pharmacopeia.
[a]The quantity of H3B-6545 drug substance is adjusted as per potency adjustment factor, a derived from the assay value in free form.
[b]Compounding amount of lactose monohydrate is adjusted depending on the quantity of H3B-6545 drug substance in order to maintain constant weight of tablet.
[c]Removed during drying process.
[d]Adjusted proportionally to the yield of milled granules.
[e]Components and composition of OPADRY 03H420000 YELLOW are described in Table.
[f]Removed during coating process.

TABLE 5

| Components of OPADRY ® 03H420000 YELLOW | |
|---|---|
| Component | Specification |
| Hypromellose | USP, Ph. Eur., JP |
| Talc | USP, Ph. Eur., JP |
| Titanium dioxide | USP, Ph. Eur., JP |
| Propylene glycol | USP, Ph. Eur., JP |
| Ferric oxide (Yellow) | NF, JPE, EC Regulation |

EC Regulation = European Commission Regulation, JP = Japanese Pharmacopoeia, JPE = Japanese Pharmaceutical Excipients, NF = National Formulary (U.S.), Ph. Eur. = European Pharmacopoeia, USP = U.S. Pharmacopeia.

Tablets were formed in the following manner:

Lactose monohydrate, low-substituted hydroxypropyl cellulose, hypromellose, and colloidal silicon dioxide were charged into a wet high-shear granulator and mixed to form a first mixture. H3B-6545 drug substance and the first mixture were then charged into a convection mixer and mixed to form a second mixture.

The second mixture was continuously fed into a wet high-shear granulator and granulated with purified water poured using a pump to form wet granules. The wet granules were continuously dried using a fluid bed dryer at elevated temperature until the loss on drying of the dried granules reached not more than 1.5%.

The dried granules were then milled with use of a screening mill. The milled granules, microcrystalline cellulose, and magnesium stearate are then charged into a convection mixer and mixed to form blended granules that were compressed into core tablets. A coating suspension (prepared by suspending the coating agent in purified water) was then sprayed onto the core tablets using a pan coating machine.

Blood samples were collected at the planned time points from each patient and centrifuged. The plasma portion of each sample was then transferred to a K2EDTA tube, which was then shipped to a bioanalytical lab for concentration measurement using LC-MS/MS. The concentration data were then analyzed using Phoenix® WinNonlin software to obtain PK parameters. The obtained PK parameters were further summarized using analytical software.

Blood samples (approximately 5 mL each) were collected from human patients pre-dose and at various hourly time points post-dose. Plasma concentrations of H3B-6545 were determined using a validated high-performance liquid chromatography/tandem mass spectrometry (LC-MS/MS) method. The lower limit of quantification was 0.100 ng/mL.

The PK Analysis Set included subjects who received H3B-6545 drug product in capsules or tablets and had sufficient evaluable plasma concentration data to derive at least 1 primary PK parameter in each treatment. Plasma concentrations of H3B-6545 (as free base) were tabulated and summarized at each nominal time using descriptive statistics (number of subjects, arithmetic mean with standard deviation [SD], coefficient of variation [CV %], geometric mean, median, minimum, and maximum) as appropriate. Individual and mean (±SD) plasma concentration-time profiles were provided for each treatment.

Pharmacokinetic parameters of H3B-6545 were calculated using noncompartmental methods, using an appropriate model for plasma data and extravascular administration. The PK parameters included, but were not limited to, area under the curve to the time of the last quantifiable concentration ($AUC_{0-t}$), maximum concentration ($C_{max}$), and time at which the maximum concentration occurred ($t_{max}$). If data permitted, the area under the plasma concentration-time curve extrapolated to infinity ($AUC_{0-inf}$), terminal elimination half-life ($t_{1/2}$), apparent total body clearance (CL/F), total systemic clearance after oral administration at steady state (CLss/F), apparent volume of distribution during the terminal phase (Vz/F), apparent steady-state volume of distribution (Vss), accumulation ratio for $C_{max}$ ($RC_{max}$) and accumulation ratio of $AUC_{0-24}$ (RAUC) were also derived.

Example 3: First Interim Analysis of Pharmacokinetics (PK) of Capsules in Fasted Patients Example 3 reports Clinical and Genomics Analysis of a single trial. The Study Population in Example 3 was as follows:

Women ≥18 years old with locally advanced or metastatic ER+HER2−BC.

Progression on at least one hormonal therapy and at least one additional therapy/regimen; no maximum number of prior lines of therapy.

ECOG performance status of 0 or 1.

Adequate bone marrow and organ function.

Excluded if had bone-only disease or inflammatory BC.

Methods were used to analyze whether H3B-6545 inactivates both wild-type and mutant ERα by targeting cysteine 530 and enforcing a unique antagonist conformation. Methods: Women with locally advanced or metastatic HR+BC are treated (tx) with H3B-6545 drug product administered once daily orally by capsule over a 28 day cycle after progression on at least one hormonal therapy and at least one additional therapy/regimen. Dose escalation uses a 3+3 design with the option to backfill previously cleared doses and allows for intrapatient dose escalation. This example explored the safety, pharmacokinetics and pharmacodynamics of H3B-6545 in women with HR+BC to identify a recommended subsequent dose for testing.

Results: As of 10 Dec. 2018, 32 patients had been treated with H3B-6545 drug product at doses of 100 to 450 mg/day; 97% had prior treatment with a CDK4/6 inhibitor and 56% had received ≥3 lines of prior anti-cancer therapy. No dose-limiting toxicities and only one Grade 3 treatment related adverse event (TRAE) were been observed (lymphocyte count decrease).

The most common (≥10%) TRAEs included asymptomatic sinus bradycardia, diarrhea, nausea, fatigue, anemia, decreased appetite, and hot flush. H3B-6545 was rapidly absorbed with a $t_{max}$ of 2-4 hours. Plasma concentration increased with dose from 100 to 450 mg, and was similar on CiD1 and CDi15. Consistent with the H3B-6545 mechanism of action and preclinical data, H3B-6545 inhibited ER target gene expression and shows a 50% decrease in Ki67 levels across all dose levels post-treatment ESR1 (60%) and PIK3CA (34%) mutations were detected in plasma at baseline and changes in mutant allele frequencies show correlation in response to treatment. Stable disease was observed in 15 patients (47%) and 34% of patients completed at least 6 months of treatment Partial responses (PRs) were observed in 3 patients: 1 patient (mutant) received 2 prior lines of therapy and 2 patients (1 mutant and 1 wild-type) received >5 prior lines of therapy including fulvestrant and capecitabine; all 3 patients received a prior CDK4/6 inhibitor.

H3B-6545 drug product was well-tolerated up to the 450 mg dose level with early signs of single-agent anti-tumor activity in a post CDK4/6 setting. Dose escalation continued in patients with advanced HER2-negative breast cancer.

Drug Administration and Dosage:

H3B-6545 administered once daily orally over a 28 day cycle.

Dose escalation using a standard 3+3 study design using dose cohorts of 100, 200, 300, 450, and 600 mg QD.

Patients allowed to backfill previously cleared doses.

Intra-patient dose escalation allowed after completion of Cycle 3.

Results (as of Apr. 20, 2019)

Patient Population:

46 patients were treated with H3B-6545 at doses of 100 to 600 mg QD.

42 (91.3%) patients received a prior CDK4/6 inhibitor and 32 (69.6%) prior fulvestrant.

30 (65.2%) patients received ≥3 prior anti-cancer therapy lines in the advanced/metastatic setting.

Demographic and baseline characteristics are shown in Table 6.

Safety:

Two dose-limiting toxicity (DLT)s, Grade 3 fatigue and Grade 3 rash morbilliform, occurred in the 600 mg QD cohort Most common (≥10%) treatment-related adverse events (TRAE) include sinus bradycardia, nausea, fatigue, anaemia, diarrhoea, and aspartate aminotransferase (Table 2).

Six Grade 3 TRAEs were observed: syncope and electrocardiogram QT prolonged at 450 mg; anaemia, aspartate aminotransferase increased, fatigue, and rash morbilliform occurred at 600 mg.

There were no TRAEs ≥Grade 4.

The most common TRAE, sinus bradycardia, does not appear to be dose- or concentration-dependent and did not require dose reductions, interruptions or discontinuations.

TRAEs are summarized in Table 7.

TABLE 6

| Category | 100 mg QD (N = 6) | 200 mg QD (N = 12) | 300 mg QD (N = 11) | 450 mg QD (N = 10) | 600 mg QD (N = 7) | Total (N = 46) |
|---|---|---|---|---|---|---|
| Age (years)[a] | | | | | | |
| n | 6 | 12 | 11 | 10 | 7 | 46 |
| Mean (SD) | 67.3 (5.75) | 55.6 (12.26) | 56.4 (14.10) | 57.5 (11.06) | 62.3 (15.32) | 58.7 (12.51) |
| Min, Max | 62, 77 | 41, 81 | 31, 75 | 38, 72 | 33, 80 | 31, 81 |
| Race, n (%) | | | | | | |
| White | 6 (100.0) | 9 (75.0) | 10 (90.9) | 10 (100.0) | 7 (100.0) | 42 (91.3) |
| Black or African American | 0 (0.0) | 1 (8.3) | 1 (9.1) | 0 (0.0) | 0 (0.0) | 2 (4.3) |
| Other | 0 (0.0) | 2 (16.7) | 0 (0.0) | 0 (0.0) | 0 (0.0) | 2 (4.3) |
| Number of Previous Anti-cancer Regimens, n (%) | | | | | | |
| 1 | 0 (0.0) | 3 (25.0) | 2 (18.2) | 3 (30.0) | 1 (14.3) | 9 (19.6) |
| 2 | 2 (33.3) | 3 (25.0) | 1 (9.1) | 0 (0.0) | 1 (14.3) | 7 (15.2) |
| 3 | 0 (0.0) | 1 (8.3) | 2 (18.2) | 1 (10.0) | 0 (0.0) | 4 (8.7) |
| 4 | 0 (0.0) | 3 (25.0) | 2 (18.2) | 2 (20.0) | 0 (0.0) | 7 (15.2) |
| 5 | 1 (16.7) | 0 (0.0) | 0 (0.0) | 2 (20.0) | 3 (42.9) | 6 (13.0) |
| ≥6 | 3 (50.0) | 2 (16.7) | 4 (36.4) | 2 (20.0) | 2 (28.6) | 13 (28.3) |
| Previous Anti-cancer Medication Groups, n (%) | | | | | | |
| Fulvestrant | 6 (100.0) | 7 (58.3) | 7 (63.6) | 7 (70.0) | 5 (71.4) | 32 (69.6) |
| Aromatase Inhibitor | 5 (83.3) | 10 (83.3) | 9 (81.8) | 9 (90.0) | 7 (100.0) | 40 (87.0) |
| CDK4/6 Inhibitor | 6 (100.0) | 9 (75.0) | 11 (100.0) | 10 (100.0) | 6 (85.7) | 42 (91.3) |
| Other | 6 (100.0) | 11 (91.7) | 9 (81.8) | 7 (70.0) | 7 (100.0) | 40 (87.0) |
| Site of Metastasis[b], n (%) | | | | | | |
| Brain | 0 (0.0) | 0 (0.0) | 1 (9.1) | 0 (0.0) | 0 (0.0) | 1 (2.2) |
| Bone | 6 (100.0) | 8 (66.7) | 8 (72.7) | 8 (80.0) | 6 (85.7) | 36 (78.3) |
| Breast | 2 (33.3) | 3 (25.0) | 2 (18.2) | 2 (20.0) | 1 (14.3) | 10 (21.7) |
| Liver | 4 (66.7) | 6 (50.0) | 9 (81.8) | 7 (70.0) | 5 (71.4) | 31 (67.4) |
| Lung | 1 (16.7) | 2 (16.7) | 6 (54.5) | 5 (50.0) | 2 (28.6) | 16 (34.8) |
| Kidney | 0 (0.0) | 0 (0.0) | 1 (9.1) | 0 (0.0) | 0 (0.0) | 1 (2.2) |
| Lymph Node | 5 (83.3) | 5 (41.7) | 3 (27.3) | 5 (50.0) | 3 (42.9) | 21 (45.7) |
| Peritoneum/Omentum | 1 (16.7) | 1 (8.3) | 2 (18.2) | 2 (20.0) | 2 (28.6) | 8 (17.4) |
| Other | 3 (50.0) | 6 (50.0) | 3 (27.3) | 4 (40.0) | 2 (28.6) | 18 (39.1) |

[a]Age is age at Informed Consent.

[b]If a subject has multiple sites in the same category, the subject is only counted once in that category.

TABLE 7

| Treatment-Related Adverse Events ≥10% | | | | | | |
|---|---|---|---|---|---|---|
| Preferred Term | 100 mg QD (N = 6) | 200 mg QD (N = 12) | 300 mg QD (N = 11) | 450 mg QD (N = 10) | 600 mg QD (N = 7) | Total (N = 46) |
| Subjects with any TRAE | 4 | 6 | 9 | 9 | 5 | 33 |
| Sinus bradycardia | 0 | 2 | 7 | 3 | 0 | 12 |
| Nausea | 1 | 0 | 3 | 4 | 1 | 9 |
| Fatigue | 1 | 2 | 3 | 1 | 1 | 8 |
| Anaemia | 0 | 1 | 2 | 3 | 1 | 7 |
| Diarrhoea | 1 | 1 | 2 | 3 | 0 | 7 |
| Aspartate aminotransferase increased | 0 | 1 | 1 | 1 | 2 | 5 |

Pharmacokinetics:

- $t_{max}$ was 2 to 4 h
- Plasma concentration increased with dose (100 to 600 mg) (FIG. 1).
- Plasma concentration was similar between C1D1 and C1D15.

Pharmacodynamics:

- ESR1 (55%) and PIK3CA (39%) mutations were detected in baseline plasma.
- Changes in mutant allele frequencies show correlation to clinical response.

Patient Case Study:

One patient, a 50 year-old female first diagnosed with ER+HER2− breast cancer in 2006, had prior treatments in the metastatic setting including letrozole/palbociclib, entinostat/exemestane, capecitabine, eribulin, and carboplatin/gemcitabine. ESR1 Y537S and PI3KCA E545K mutations were detected in baseline tumor and plasma. At the time of enrollment, ECOG performance status was 1; sites of disease included liver, bone, pleural effusion, pelvic ascites and subcutaneous nodules. H3B-6545 was initiated at a dose of 450 mg QD in June 2018.

The decrease in the sum of the diameters of all target lesions from baseline to C3D1 and C7D1 was −27.8% and −35.6%, respectively. After 4 cycles, the patient achieved partial response and remained on treatment in C11.

Figure 2:
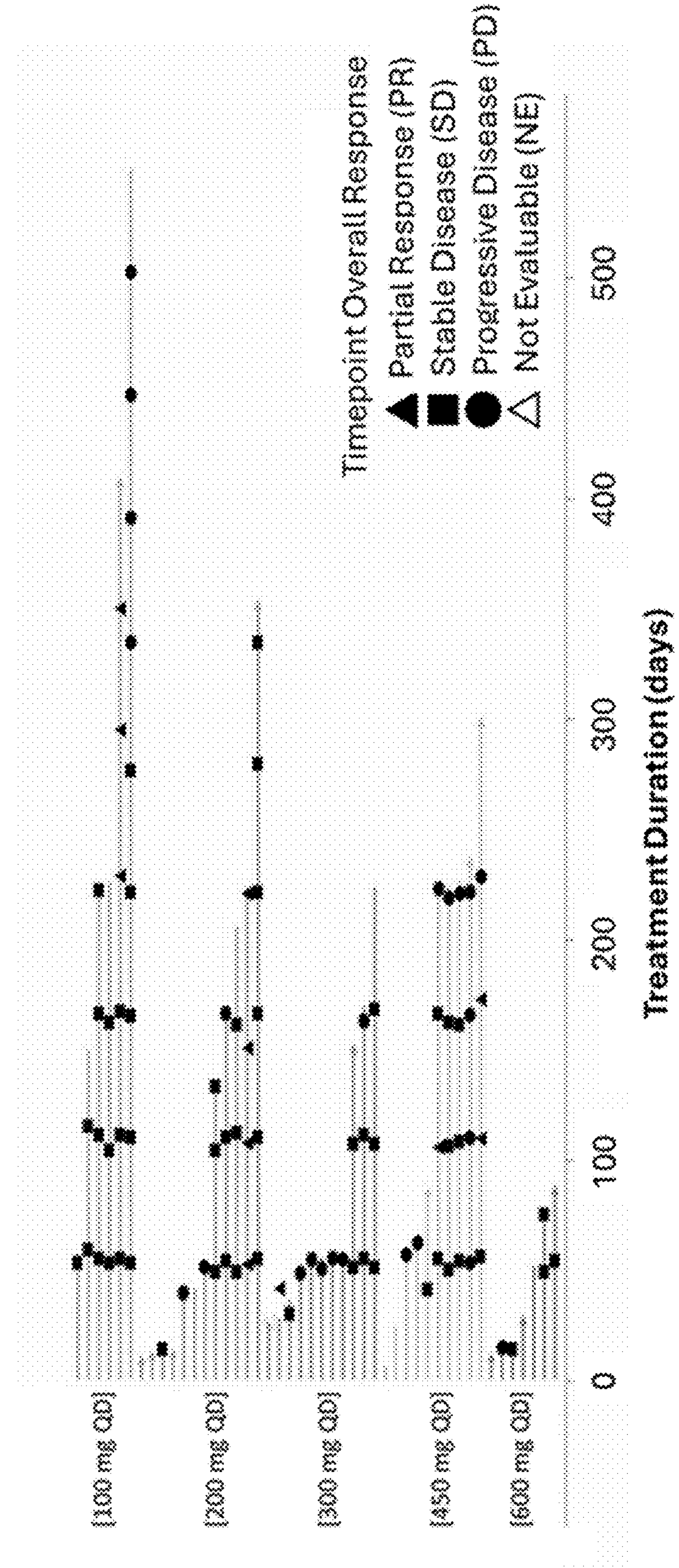
FIG. 2 shows tumor response and duration of H3B-6545 treatment as reported in Example 3. Partial response, stable response, progressive disease, and no evaluable are shown at each tumor assessment. Arrows represent treatment ongoing at time of data cut.
Figure 3:
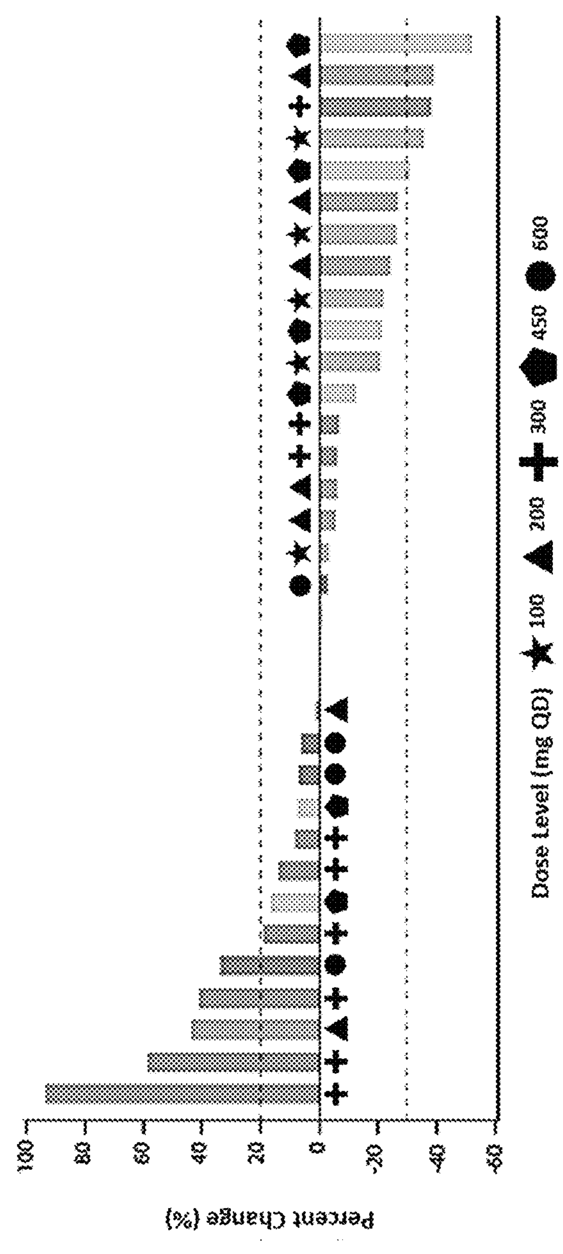
FIG. 3 shows percent change in sum of diameter of target lesions as reported in Example 3.

Preliminary Activity:

- Stable disease was observed in 17 (37.0%) patients
- At least 6 months of therapy was completed by 14 (30.4%) patients
- Confirmed partial response was observed in 3 (6.5%) patients Further information on preliminary activity is shown in FIG. 2. FIG. 3 shows percent change in sum of diameters of target lesions.

Table 8 shows tumor Response and Progression-Free Survival.

TABLE 8

| | 100 mg QD (N = 6) | 200 mg QD (N = 12) | 300 mg QD (N = 11) | 450 mg QD (N = 10) | 600 mg QD (N = 7) | Total (N = 46) |
|---|---|---|---|---|---|---|
| Best Overall Response (BOR), n (%) | | | | | | |
| Complete Response (CR) | 0 (0.0) | 0 (0.0) | 0 (0.0) | 0 (0.0) | 0 (0.0) | 0 (0.0) |
| Partial Response (PR) | 1 (16.7) | 1 (8.3) | 0 (0.0) | 1 (10.0) | 0 (0.0) | 3 (6.5) |
| Stable Disease (SD) | 5 (83.3) | 4 (33.3) | 3 (27.3) | 3 (30.0) | 2 (28.6) | 17 (37.0) |
| Progressive Disease (PD) | 0 (0.0) | 2 (16.7) | 5 (45.5) | 3 (30.0) | 1 (14.3) | 11 (23.9) |
| Not Evaluable (NE) | 0 (0.0) | 4 (33.3) | 3 (27.3) | 3 (30.0) | 4 (57.1) | 14 (30.4) |
| Unknown (UNK) | 0 (0.0) | 1 (8.3) | 0 (0.0) | 0 (0.0) | 0 (0.0) | 1 (2.2) |
| Objective Responses (CR + PR), n(%) | 1 (16.7) | 1 (8.3) | 0 (0.0) | 1 (10.0) | 0 (0.0) | 3 (6.5) |
| 95% CI of Objective Response Rate (ORR)[a] | (0.4, 64.1) | (0.2, 38.5) | (0.0, 28.5) | (0.3, 44.5) | (0.0, 41.0) | (1.4, 17.9) |
| Progressive-Free Survival (months)[b] | | | | | | |
| Median (95% CI) | 9.3 (7.4, NE) | 5.5 (0.9, NE) | 1.8 (1.6, 5.4) | 7.2 (1.8, 7.3) | NE (0.5, NE) | 7.2 (1.9, 7.4) |

TABLE 8-continued

| | 100 mg QD (N = 6) | 200 mg QD (N = 12) | 300 mg QD (N = 11) | 450 mg QD (N = 10) | 600 mg QD (N = 7) | Total (N = 46) |
|---|---|---|---|---|---|---|
| Q1 (95% CI) | 7.5 (7.4, 11.0) | 1.5 (0.9, 5.5) | 1.8 (1.6, 1.8) | 1.9 (1.8, 7.2) | NE (0.5, NE) | 1.8 (1.6, 2.1) |
| Q3 (95% CI) | NE (7.4, NE) | NE (1.7, NE) | 5.4 (1.8, NE) | 7.3 (2.1, 7.5) | NE (0.5, NE) | 7.5 (7.3, NE) |

Conclusions

Safety/Tolerability: Most TRAEs were grade 1 or 2 and manageable; tolerated up to and including 450 mg QD.

Pharmacodynamic: Changes in mutant allele frequencies show correlation to clinical response.

Preliminary activity: Encouraging signal of anti-tumor activity was observed in a heavily pre-treated, post CDK4/6i setting including 3 confirmed partial responses and mPFS=7.2 months.

Phase 2: To be initiated following determination of RP2D.

Example 4: Second Interim Analysis

The clinical trial of Example 3 was continued and PK evaluations (of this Example 4) were made at a later date on the basis of a larger patient population. The summary of Tables 1 in Analysis of Pharmacokinetic (PK) of Capsules in Fasted Patients and 2 show PK parameters and profiles of human patients receiving capsules of H3B-6545 drug product prepared as in Example 1. Patients received a total equivalent dosage of 100 mg, 200 mg, 300 mg, 450 mg or 600 mg of Formula I, as identified in the table. Table 1 reflects PK values for patients as measured on the first day of their first cycle. Table 2 reflects PK values for patients as measured on the fifteenth day of their first cycle.

The PK parameters were calculated after administration to a human subjects in need thereof, wherein the human subjects were in a fasted condition. QD means that the dose was administered "quaque die" or only once per day. The parameter n is the number of human subjects in need thereof that were administered the respective doses.

Tables 9 and 11 include the geometric means and the geometric means coefficients of variation for all the plasma PK parameters, except $T_{max}$ and $T_{lag}$, associated with each dose, said PK parameters being calculated from the human subjects in need thereof (n). $T_{max}$ and $T_{lag}$ values include the median value calculated amongst the human subjects in need thereof in addition to the minimum and maximum values. Tables 10 and 12 have normalized the AUC0-t, AUC0-24, AUC0-inf and Cmax PK parameters illustrated in Table 9 and Table 11 to plasma PK parameters per 1 mg of active pharmaceutical ingredient (API).

TABLE 9

| Plasma PK Parameters[a] | Units | Cycle 1 Day 1-Dose Escalation H3B-6545 100 mg QD | H3B-6545 200 mg QD | H3B-6545 300 mg QD | H3B-6545 450 mg QD | H3B-6545 600 mg QD |
|---|---|---|---|---|---|---|
| $AUC_{0-t}$ | h * ng/mL | 1679 (85.4); 6 | 4812 (71.8); 12 | 9525 (62.9); 11 | 16177 (43.2); 11 | 22302 (64.5); 7 |
| $AUC_{0-24}$ | h * ng/mL | 1678 (85.2); 6 | 4761 (71); 12 | 9482 (60.8); 11 | 16170 (42.7); 11 | 22370 (63.3); 7 |
| $AUC_{0-inf}$ | h * ng/mL | 2132 (92.2); 6 | 5274 (68.3); 8 | 11077 (49.1); 10 | 22976 (42.4); 8 | 32853 (68.6); 5 |
| $C_{max}$ | ng/mL | 178 (85.3); 6 | 473 (72); 12 | 898 (66.2); 11 | 1501 (53.1); 11 | 2048 (62); 7 |
| $T_{max}$[b] | h | 3.05 (2-6); 6 | 5 (2-25.1); 12 | 4 (2-24.8); 11 | 4 (2-10); 11 | 4 (2-23.37); 7 |
| $T_{lag}$[b] | h | 0 (0-1); 6 | 0 (0-0.6); 12 | 0 (0-0.58); 11 | 0 (0-0.5); 11 | 0 (0-0.5); 7 |
| $t_{1/2}$ | h | 10.2 (21.4); 6 | 9.73 (29.9); 8 | 9.58 (51.3); 10 | 11.0 (35.6); 8 | 13.1 (21.3); 5 |
| CL/F | L/h | 46.9 (92.2); 6 | 37.9 (68.3); 8 | 27.1 (49.1); 10 | 19.6 (42.4); 8 | 18.3 (68.6); 5 |
| Vz/F | L | 689 (86.2); 6 | 532 (70.4); 8 | 374 (61.3); 10 | 311 (43.7); 8 | 344 (77.9); 5 |
| Vss | L | 713 (75.3); 6 | 567 (60.6); 8 | 416 (59.5); 10 | 343 (42.5); 8 | 366 (73.1); 5 |

[a]Geometric Mean (GeoCV %); n

[b]Median (Min, Max); n

TABLE 10

| Plasma PK Parameter (per 1 mg of API) | Units | Cycle 1 Day-Dose Escalation H3B-6545 100 mg QD | H3B-6545 200 mg QD | H3B-6545 300 mg QD | H3B-6545 450 mg QD | H3B-6545 600 mg QD |
|---|---|---|---|---|---|---|
| $AUC_{0-t}$ | h * ng/mL/mg | 16.8 | 24.1 | 31.8 | 35.9 | 37.2 |
| $AUC_{0-24}$ | h * ng/mL/mg | 16.8 | 23.8 | 31.6 | 35.9 | 37.3 |
| $AUC_{0-inf}$ | h * ng/mL/mg | 21.3 | 26.37 | 36.9 | 51.1 | 54.8 |
| $C_{max}$ | ng/mL/mg | 1.78 | 2.4 | 3.0 | 3.3 | 3.4 |

TABLE 11

| Plasma PK Parameters[a] | Units | Cycle 1 Day 15-Dose Escalation H3B-6545 100 mg QD | H3B-6545 200 mg QD | H3B-6545 300 mg QD | H3B-6545 450 mg QD | H3B-6545 600 mg QD |
|---|---|---|---|---|---|---|
| $AUC_{0-t}$ | h * ng/mL | 2589 (57.4); 6 | 6910 (53.1); 10 | 12081 (51.7); 11 | 14053 (53.2); 10 | 18741 (80.9); 3 |
| $AUC_{0-24}$ | h * ng/mL | 2559 (56.2); 6 | 6872 (52.8); 10 | 12009 (51); 11 | 14023 (52.6); 10 | 18366 (78.1); 3 |
| $AUC_{0-inf}$ | h * ng/mL | 2947 (55.4); 5 | 7953 (58); 8 | 12747 (55.6); 9 | 17391 (49.7); 9 | 39731 (101.6); 3 |
| $C_{max}$ | ng/mL | 287 (31.3); 6 | 605 (56); 10 | 1201 (38.2); 11 | 1415 (53.5); 10 | 1683 (98.7); 3 |
| $T_{max}^{b}$ | h | 2 (2-8.03); 6 | 2.17 (2-6); 10 | 4 (2-5.95); 11 | 4 (1-8); 10 | 4 (4-6); 3 |
| $T_{lag}^{b}$ | h | 0 (0-0); 6 | 0 (0-0); 10 | 0 (0-0); 11 | 0 (0-0); 10 | 0 (0-0); 3 |
| $t_{1/2}$ | h | 11.5 (23.1); 5 | 10.1 (27.7); 8 | 8.52 (35.9); 9 | 9.81 (50.4); 9 | 21.8 (146.9); 3 |
| CLss/F | L/h | 39.1 (56.2); 6 | 29.1 (52.8); 10 | 26.2 (50.5); 10 | 32.1 (52.6); 10 | 32.7 (78.1); 3 |
| Vz/F | L | 731 (57); 5 | 455 (69.4); 8 | 348 (37.1); 9 | 466 (98.2); 9 | 1030 (282.1); 3 |
| Vss | L | 679 (49.3); 5 | 456 (61.2); 8 | 373 (39.3); 9 | 489 (86.7); 9 | 1100 (230.8); 3 |
| $RC_{max}$ | | 1.61 (69.3); 6 | 1.28 (118.2); 10 | 1.34 (38.3); 11 | 1.05 (42.1); 10 | 0.685 (69.2); 3 |
| RAUC | | 1.52 (58.3); 6 | 1.43 (72.9); 10 | 1.27 (38.3); 11 | 0.920 (49); 10 | 0.712 (31.4); 3 |

[a]Geometric Mean (GeoCV %); n
[b]Median (Min, Max); n

TABLE 12

| Plasma PK Parameters (per 1 mg of API) | Units | Cycle 1 Day 15-Dose Escalation H3B-6545 100 mg QD | H3B-6545 200 mg QD | H3B-6545 300 mg QD | H3B-6545 450 mg QD | H3B-6545 600 mg QD |
|---|---|---|---|---|---|---|
| $AUC_{0-t}$ | h * ng/mL/mg | 25.9 | 34.6 | 40.3 | 31.2 | 31.2 |
| $AUC_{0-24}$ | h * ng/mL/mg | 25.6 | 34.4 | 40.0 | 31.2 | 30.6 |
| $AUC_{0-inf}$ | h * ng/mL/mg | 29.5 | 39.8 | 42.5 | 38.6 | 66.2 |
| $C_{max}$ | ng/mL/mg | 2.9 | 3.0 | 4.0 | 3.1 | 2.8 |

Example 5: Pharmacokinetics (PK) of 450 mg Capsules in Fasted and Fed Patients Table 3 details PK parameters and profiles of human patients receiving capsules prepared as in Example 1. Patients received a total equivalent dosage of 450 mg of Formula I, as identified in Table 13. Table 14 has normalized the AUC0-t, AUC0-24, AUC0-inf and Cmax PK parameters illustrated in Table 13 to plasma PK parameters per 1 mg of active pharmaceutical ingredient (API).

TABLE 13

| Plasma PK Parameters[a] | Units | H3B-6545 450 mg QD-Dose Expansion-Fasted | H3B-6545 450 mg QD-Dose Expansion-Fed |
|---|---|---|---|
| $AUC_{0-t}$ | h * ng/mL | 12464 (65.9); 18 | 16101 (97.3); 17 |
| $AUC_{0-24}$ | h * ng/mL | 12252 (65.4); 18 | 19473 (61.2); 15 |
| $AUC_{0-inf}$ | h * ng/mL | 16457 (64.1); 16 | 25546 (51.9); 8 |
| $C_{max}$ | ng/mL | 1093 (81.6); 18 | 1561 (54.5); 17 |
| $T_{max}^{b}$ | h | 4 (1-6.15); 18 | 6 (4-10); 17 |
| $T_{lag}^{b}$ | h | 0 (0-0); 18 | 0 (0-0); 17 |
| $t_{1/2}$ | h | 10.9 (37.9); 16 | 8.83 (30.8); 8 |
| CLss/F | L/h | 36.7 (65.4); 18 | 20.5 (42.7); 13 |
| Vz/F | L | 566 (92.8); 16 | 279 (37.8); 8 |
| Vss | L | 597 (89.5); 16 | 350 (38.9); 8 |

[a]Geometric Mean (GeoCV %); n
[b]Median (Min, Max); n

TABLE 14

| Plasma PK Parameters (per 1 mg of API) | Units | H3B-6545 450 mg QD-Dose Expansion-Fasted | H3B-6545 450 mg QD-Dose Expansion-Fed |
|---|---|---|---|
| $AUC_{0-t}$ | h * ng/mL/mg | 27.7 | 35.8 |
| $AUC_{0-24}$ | h * ng/mL/mg | 27.2 | 43.3 |
| $AUC_{0-inf}$ | h * ng/mL/mg | 36.6 | 56.8 |
| $C_{max}$ | ng/mL/mg | 2.4 | 3.5 |

Example 6: Pharmacokinetics (PK) of Tablets in Humans

Capsules as described in Example 1 and tablets as described in Example 2 were tested in healthy human subjects. All doses were well-tolerated. Similar exposure (both Cmax and AUC) and Tmax of H3B-6545 was noted between capsules and tablets, as shown in Table 15.

TABLE 15

| Plasma PK Parameters[a] | 450 mg H3B-6545 (capsule) n = 16 | 450 mg H3B-6545 (tablet) n = 16 |
|---|---|---|
| $AUC_{0-24}$ (h * ng/mL) | 12650 (58.8) | 13320 (54.9) |
| $AUC_{0-t}$ (h * ng/mL) | 15580 (58.4) | 16420 (57) |
| $AUC_{0-inf}$ (h * ng/mL) | 16560 (58.1) | 17520 (57.6) |
| $C_{max}$ (ng/mL) | 1069 (56.6) | 1122 (46.1) |
| $t_{max}^{b}$ (h) | 3.03 (1.00-6.00) | 4.00 (1.00-10.0) |
| $t_{1/2}$ (h) | 10.95 (21.4) | 11.01 (21.7) |

TABLE 15-continued

| Plasma PK Parameters[a] | 450 mg H3B-6545 (capsule) n = 16 | 450 mg H3B-6545 (tablet) n = 16 |
|---|---|---|
| CL/F (L/h) | 27.17 (58.1) | 25.69 (57.6) |
| $V_z$/F (L) | 429.0 (63.7) | 408.0 (59.2) |

[a]Geometric Mean (GeoCV %),
[b]Median (Min-Max)

Relative bioavailability of the capsule vs. tablet formulations of H3B-6545 is shown in Table 16.

TABLE 16

| Parameter | Tablet Geo. LSM (reference) | Capsule Geo. LSM (test) | Ratio of Geo. LSM (%) (test: reference) | 90% CI* | Intra-subject CV % |
|---|---|---|---|---|---|
| $AUC_{0-24}$ (h * ng/mL) | 13320 | 12650 | 94.99 | (79.27, 113.83) | 29.7 |
| $AUC_{0-t}$ (h * ng/mL) | 16420 | 15580 | 94.86 | (79.63, 113.00) | 28.7 |
| $AUC_{0-inf}$ (h * ng/mL) | 17520 | 16560 | 94.56 | (80.10, 111.64) | 27.1 |
| $C_{max}$ (ng/mL) | 1122 | 1069 | 95.28 | (79.48, 114.21) | 29.7 |

Geo.LSM: Geometric Least Square Mean.
CI: Confidence Interval; *Column shows lower and upper boundary.
CV: Coefficient of Variation

Example 7—Genomics Study

Because of lack of effective treatment in endocrine resistant metastatic breast cancer (MBC), we developed H3B-6545, a novel selective ERa covalent antagonist, capable of irreversibly inactivating both wild-type and mutant ERa.

The aims of this study are to 1) characterize hotspot mutation profiles in heavily pretreated MBC and correlate ESR1, PIK3CA and AKT1 mutations in plasma vs tumor tissue 2) determine if mutations in ESR1 or PIK3CA predict response to H3B-6545 and 3) evaluate if longitudinal tracking of ctDNA correlates with response to H3B-6545.

Methods

Fresh plasma samples were collected at baseline (pre-dose), cycle 1 day 15 (CID15), C2D1, C3D1 and every 8 weeks thereafter with a final sample collection at disease progression. At baseline, BEAMing digital PCR was used to evaluate hotspot mutations in ESR1, PIK3CA and AKT1. Patient specific ctDNA mutations were subsequently monitored by ddPCR. Baseline tumor biopsies were subjected to a targeted Next Generation Sequencing (NGS) panel to identify hotspot mutations.

Results

In 77% of patients (30/39), mutations were detected at baseline by the BEAMing assay and of those, 21/39, 16/39 and 3/39 had mutations in ESR1, PIK3CA and AKT1, respectively. 20% (9/39) of patients exhibited co-mutations in ESR1 and PIK3CA. In 60% (9/15) of patients, DNA mutations identified by the plasma BEAMing assay were also detected in the tumor biopsy whereas; DNA mutations found in tissue were also detected in plasma in 86% (12/14) of cases. Serial ctDNA monitoring revealed that in patients with confirmed partial responses (3/3), ctDNA levels were undetectable by C2D1. In contrast, ctDNA levels increased from baseline in 3/4 patients with progressive disease. Exploration of ctDNA ratios (day 15/baseline and day 30/baseline) and correlations of PIK3CA and ESR1 mutations with response to H3B-6545 are presented.

Conclusion for Example 7 ctDNA is a reliable sample type for assessing ESR1, PIK3CA, and AKT1 mutations in MBC, overcoming the challenges of obtaining biopsies in the metastatic setting. In addition, ctDNA dynamics appear to provide a useful tool to monitor the efficacy of H3B-6545.

Drug Administration and Dosage:

H3B-6545 administered once daily orally (PO QD) over a 28-day cycle

Dose escalation using a standard 3+3 study design using dose cohorts of 100, 200, 300, 450, and 600 mg/day Liquid biopsy assays: 10 ml of Strek plasma was collected at the site and then processed into plasma at Sysmex Inostics. cfDNA was isolated from 2 ml of plasma for BEAMing and 3 ml for Biorad ddPCR Tumor next-generation sequencing (NGS) analysis: DNA from 10×5 μm slides was isolated using the Recoverall Kit, and 10 ng of DNA was then used as input for Oncomine Comprehensive Assay.

Study baseline characteristics are shown in Table 17.

TABLE 17

| Category | Total (N = 46) |
|---|---|
| Number of Previous Anti-cancer Regimens, n (%) | |
| 1 | 9 (19.6) |
| 2 | 7 (15.2) |
| 3 | 4 (8.7) |
| ≥4 | 26 (56.5) |
| Previous Anti-cancer Medication Groups, n (%) | |
| Fulvestrant | 32 (69.6) |
| Aromatase Inhibitor | 40 (87.0) |
| CDK4/6 Inhibitor | 42 (91.3) |
| Other | 40 (87.0) |
| Last Previous Anti-cancer Medication, n (%) | |
| Fulvestrant | 10 (21.7) |
| Aromatase Inhibitor | 11 (23.9) |
| CDK4/6 Inhibitor | 20 (43.5) |
| Other | 33 (71.7) |

Figure 4:
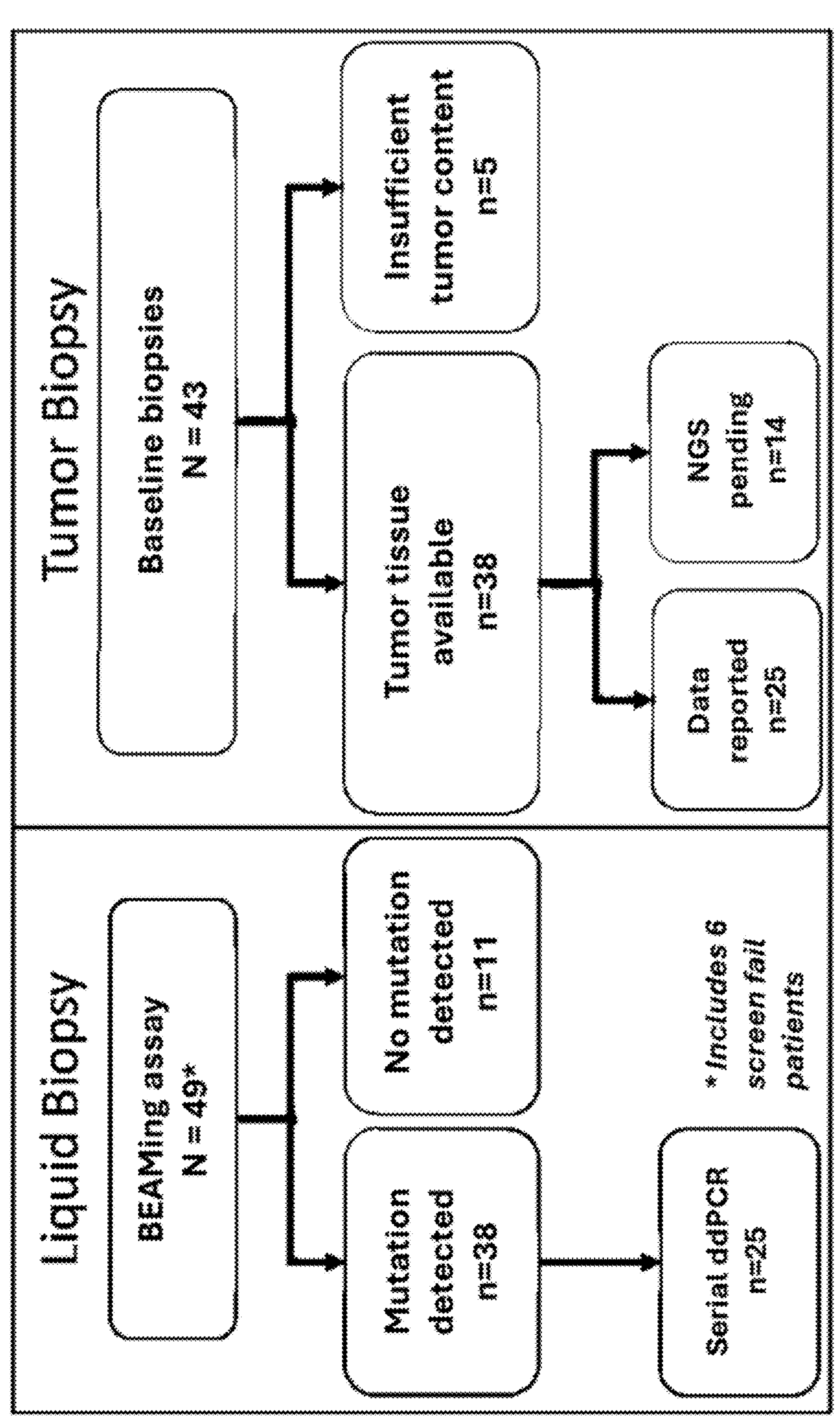
FIG. 4 shows an overview of liquid biopsy and tissue biopsy sample sets.

FIG. 4 shows an overview of liquid biopsy and tissue biopsy sample sets.

FIG. 5A-FIG. 5E show baseline genomics profile of patients in this Example. AA=amino acid. *AKT1 mutation observed in 3/49 patients (data not shown).

FIG. 5A to 5E show BEAMing assay. A. Baseline ESR1 and PIK3CA mutation status of patients; B and C. Clonalities of ESR1 and PIK3CA mutations; D and E. Amino acid distribution of PIK3CA and ESR1 mutations.

Figures 5A, 5B, 5C, 5D, 5E:
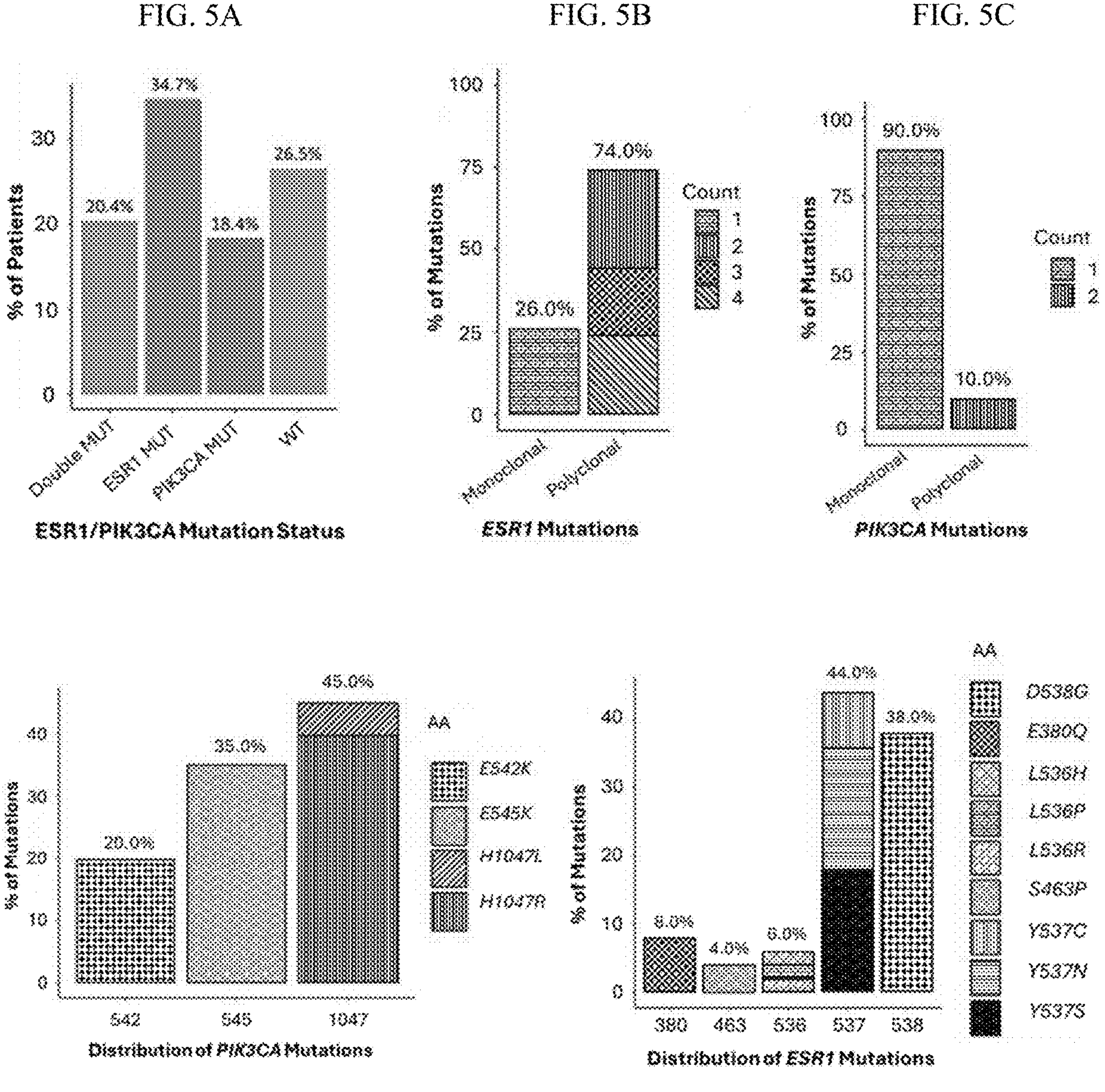
FIG. 5A-FIG. 5E show baseline genomics profile of patients in Example 7.
Figure 5F:
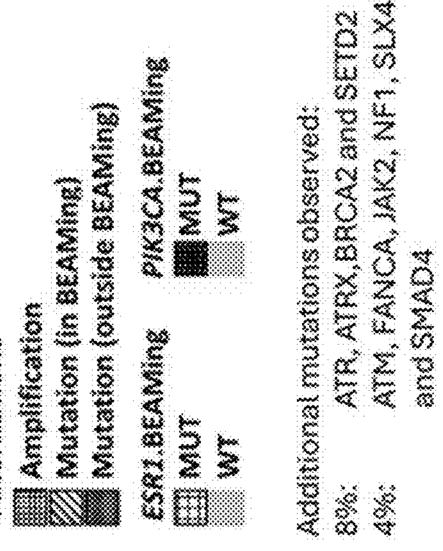
FIG. 5F shows an oncoprint of mutations found in baseline tissue biopsy as determined by Oncomine Comprehensive Panel.
Figure 5F:
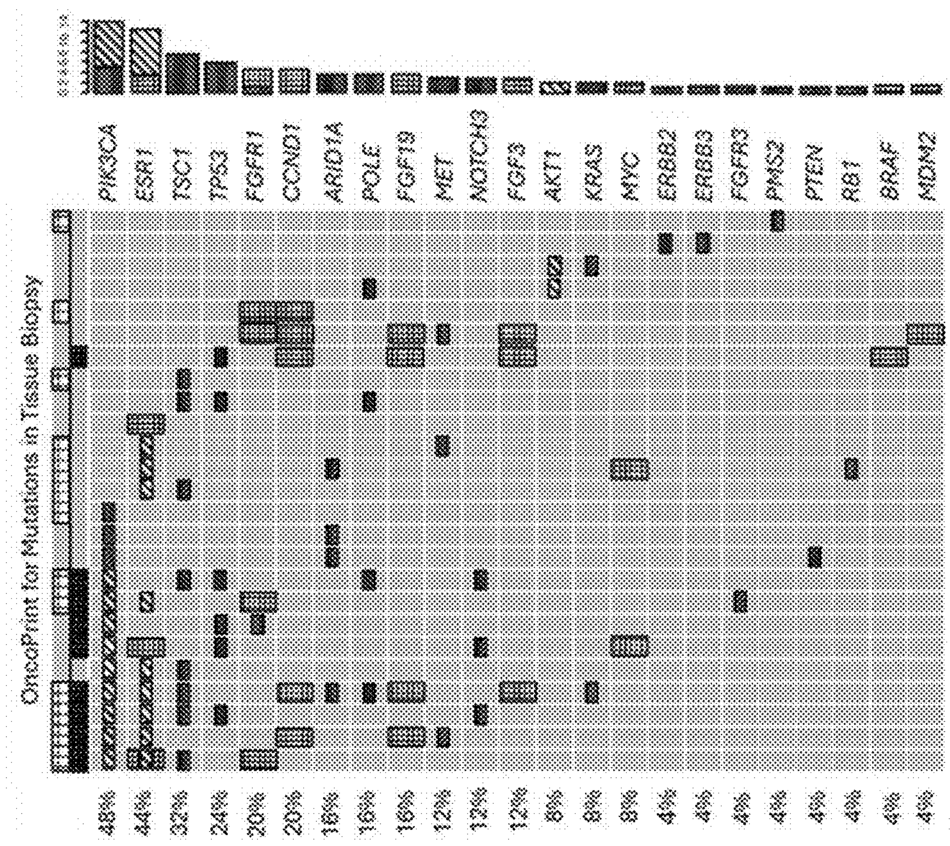

FIG. 5F shows an oncoprint of mutations found in baseline tissue biopsy as determined by Oncomine Comprehensive Panel.

Figures 6A, 6B:
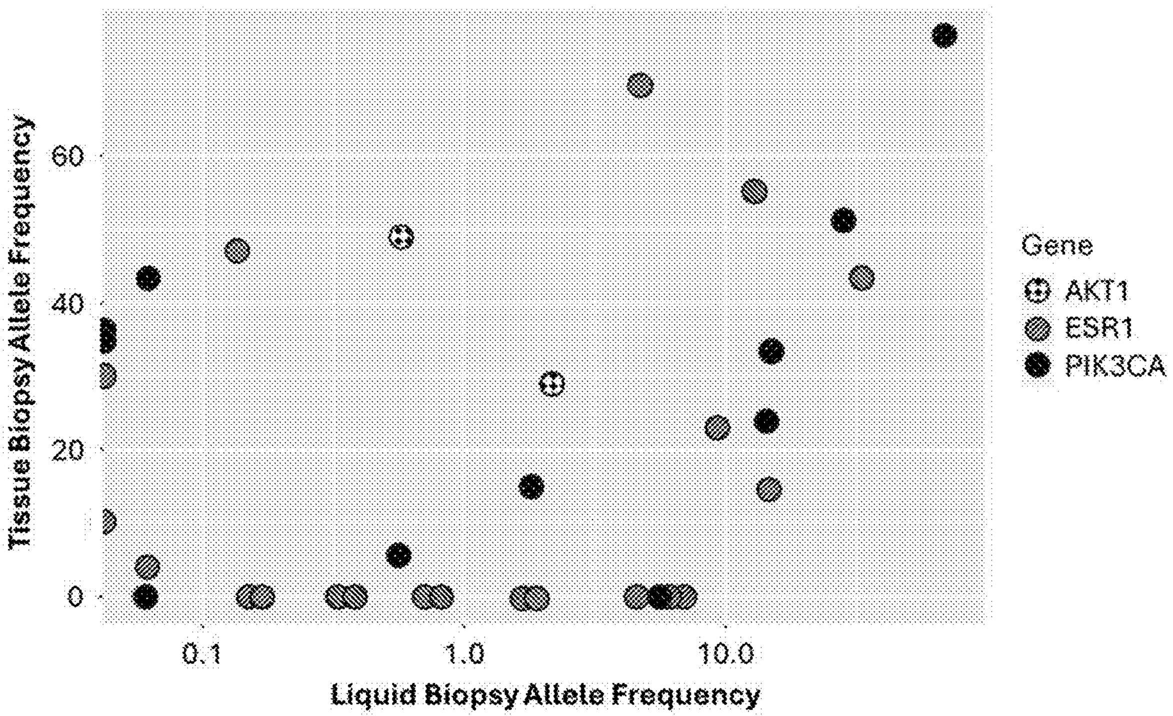
FIG. 6A and FIG. 6B show concordance of mutations found in tissue and liquid biopsies in Example 7.

FIG. 6A and FIG. 6B show concordance of mutations found in tissue and liquid biopsies in Example 2. FIG. 6A shows allele frequency distribution and concordance of tissue and liquid biopsy mutations. FIG. 6B is a summary table of tissue and liquid biopsy mutation concordance.

Figure 7A:
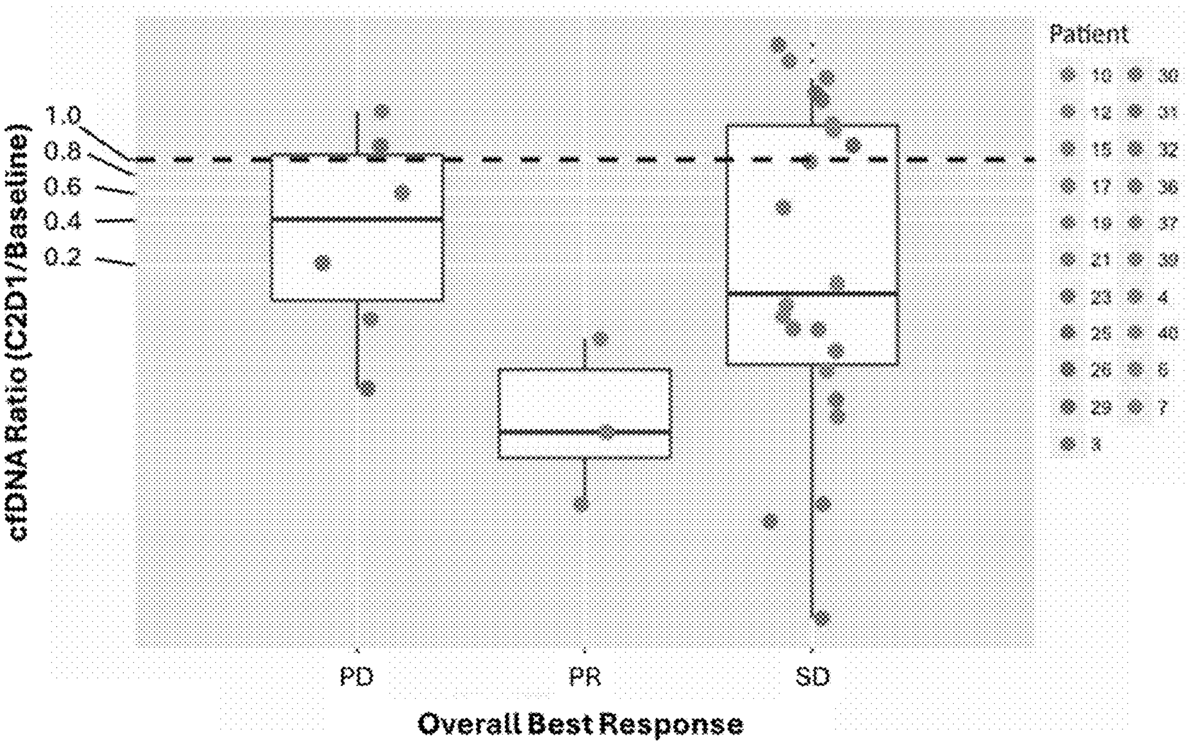
FIG. 7A-7C show ctDNA dynamics correlated with overall best response to H3B-6545. AF=allele frequency, C=cycle, D=day, PD=progressive disease, PR=partial response, SD=stable disease. Dotted line represents ddPCR assay LOD.
Figure 7B:
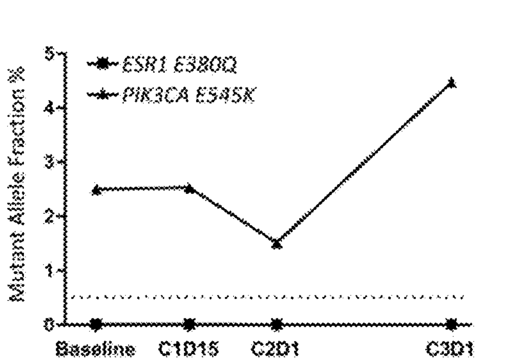
Figure 7C:
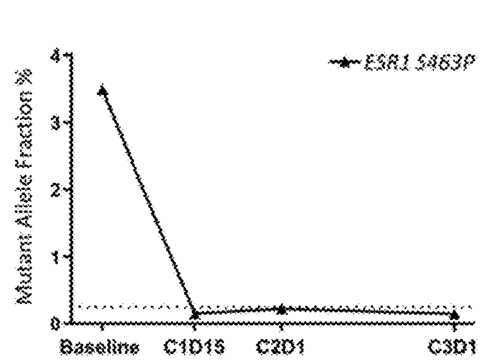

FIG. 7A-7C show ctDNA dynamics correlated with overall best response to H3B-6545.AF=allele frequency, C=cycle, D=day, PD=progressive disease, PR=partial response, SD=stable disease. Dotted line represents ddPCR assay LOD. FIG. 7A. Ratio of AF baseline/C2D1 with each patient colored separately. One patient may have multiple mutations. FIG. 7B and FIG. 7C. Example ctDNA dynamics in a patient with progressive disease (B) vs partial response (C).

Patient Case Study—This is the same patient case study reported in Example 3.

A 50 year-old female first diagnosed with ER+HER2− BC in 2006.

Prior treatments in the metastatic setting included letrozole/palbociclib, entinostat/exemestane, capecitabine, eribulin, and carboplatin/gemcitabine.

At the time of enrollment, the ECOG performance status was 1; sites of disease included liver, bone, pleural effusion, pelvic ascites and subcutaneous nodules.

ESR1 Y537S and PI3KCA E545K mutations were detected in baseline tumor and plasma.

Initiated H3B-6545 at a dose of 450 mg PO QD in June 2018.

The decrease in the sum of the diameters of all target lesions from baseline to C3D1 and C7D1 was −27.8% and −35.6%, respectively.

After 4 cycles, the patient achieved partial response and remained on treatment in C11.

Conclusions

In late-line ER+MBC, PIK3CA and ESR1 mutations were detected in baseline plasma 39% and 55%, respectively Tissue to plasma mutation level concordance was 80%.

Liquid biopsy to tissue mutation level concordance was 51%.

ctDNA levels were undetectable by C2D1 in patients with confirmed partial response.

ctDNA dynamics appear be a useful tool for monitoring efficacy of H3B-6545 and characterization of baseline genomics profiles.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An oral dosage form, wherein said oral dosage form is a capsule comprising by total weight of the capsule: 28% to 44% of a compound given by Formula I or a pharmaceutically acceptable salt thereof, wherein said Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide represented by the structure:

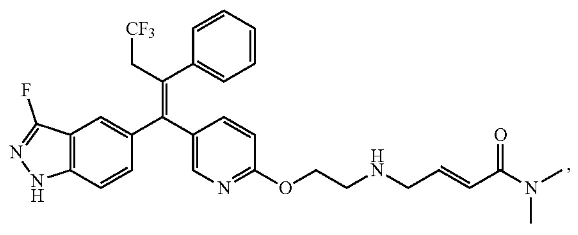 [SMILES: CN(C)C(=O)/C=C/CNCCOc1ccc(/C(=C(/CC(F)(F)F)c2ccccc2)c2ccc3[nH]nc(F)c3c2)cn1]

12% to 19% of a lactose monohydrate, 8% to 13% of a low-substituted hydroxypropyl cellulose, 1% to 5% of a microcrystalline cellulose, 0.5% to 5% of a hydroxypropyl cellulose, 0.05% to 0.5% of a colloidal anhydrous silica, and 0.1% to 1% of a magnesium stearate, wherein said oral dosage form is formulated to achieve a mean Cmax of about 1 ng/mL to about 4 ng/mL as measured for every mg of Formula I in said oral dosage form.

2. The oral dosage form of claim 1, wherein the capsule further comprises by total weight of the capsule: 18% to 44% of a hypromellose capsule shell.

3. The oral dosage form of claim 1 comprising:

(i) an internal phase comprising:

150 to 160 mg of the compound given by Formula I or the pharmaceutically acceptable salt thereof, 67 to 68 mg of the lactose monohydrate, 45 mg of the low-substituted hydroxypropyl cellulose, 15 mg of the microcrystalline cellulose, 9 mg of the hydroxypropyl cellulose, 0.6 mg of the colloidal anhydrous silica, and 1.5 mg of the magnesium stearate; and (ii) an external phase comprising 1.5 mg of the magnesium stearate.

4. The oral dosage form of claim 3, wherein the oral dosage form comprises a capsule shell, wherein the capsule shell comprises:

(i) hypromellose;

(ii) iron oxide red; and/or (iii) titanium dioxide.

5. The oral dosage form of claim 3, comprising a mono-HCl salt form of the compound given by Formula I.

6. The oral dosage form of claim 1 comprising:

i) an internal phase comprising:

50 to 60 mg of the compound given by Formula I or the pharmaceutically acceptable salt thereof, 22 to 23 mg of the lactose monohydrate, 15 mg of the low-substituted hydroxypropyl cellulose, 5 mg of the microcrystalline cellulose, 3 mg of the hydroxypropyl cellulose, 0.2 mg of the colloidal anhydrous silica, and 0.5 mg of the magnesium stearate; and ii) an external phase comprising 0.5 mg of the magnesium stearate.

7. The oral dosage form of claim 6, wherein said dosage form comprises a capsule shell, wherein said capsule shell comprises hypromellose, iron oxide red, and titanium dioxide.

8. The oral dosage form of claim 6, comprising a mono-HCl salt form of the compound given by Formula I.

9. The oral dosage form of claim 1, comprising:

i) an internal phase comprising:

25 to 30 mg of the compound given by Formula I or the pharmaceutically acceptable salt thereof, 11 to 12 mg of the lactose monohydrate, 7.5 mg of the low-substituted hydroxypropyl cellulose, 2.5 mg of the microcrystalline cellulose, 1.5 mg of the hydroxypropyl cellulose, 0.1 mg of the colloidal anhydrous silica, and 0.25 mg of the magnesium stearate; and ii) an external phase comprising 0.25 mg of the magnesium stearate.

10. The oral dosage form of claim 9, wherein said dosage form comprises a capsule shell, wherein said capsule shell comprises hypromellose, iron oxide red, and titanium dioxide.

11. The oral dosage form of claim 9, comprising a mono-HCl salt form of the compound given by Formula I.

12. An oral dosage form comprising:

(i) an internal phase comprising:

150 to 160 mg of a compound given by Formula I or a pharmaceutically acceptable salt thereof, wherein said Formula I is (E)-N,N-dimethyl-4-[2-[5-[(Z)-4,4,4-trifluoro-1-(3-fluoro-1H-indazol-5-yl)-2-phenylbut-1-enyl]pyridin-2-yl]oxyethylamino]but-2-enamide represented by the structure:

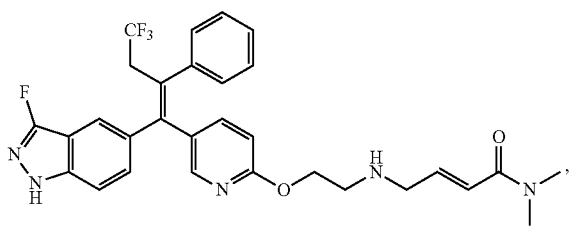 [SMILES: CN(C)C(=O)/C=C/CNCCOc1ccc(/C(=C(/CC(F)(F)F)c2ccccc2)c2ccc3[nH]nc(F)c3c2)cn1]

241 to 242 mg of a lactose monohydrate, 90 mg of a low-substituted hydroxypropyl cellulose, 18 mg of a hypromellose, and 1.2 mg of a colloidal silicon dioxide; and (ii) an external phase comprising 12 mg of a magnesium stearate and 78 mg of a microcrystalline cellulose, wherein said oral dosage form is formulated to achieve a mean Cmax of about 1 ng/mL to about 4 ng/mL as measured for every mg of Formula I in said oral dosage form.

13. The oral dosage form of claim 12, further comprising a film coating comprising hypromellose, talc, titanium dioxide, propylene glycol, ferric oxide, and purified water.

14. The oral dosage form of claim 1, comprising a mono-HCl salt form of the compound given by Formula I.

15. The oral dosage form of claim 1, wherein the dosage form is formulated to achieve a mean tmax of said mean Cmax in about 2 hours to about 7 hours.

16. The oral dosage form of claim 1, wherein said mean Cmax is in the range of 80% to 125% of 3 ng/mL to 80% to 125% of 3.5 ng/mL for every mg of Formula I in said dosage form.

17. The oral dosage form of claim 12, comprising a mono-HCl salt form of the compound given by Formula I.

18. A method of treating cancer in a human subject comprising administering to said subject the oral dosage form of claim 1.

* * * * *